(12) United States Patent
Kakuta et al.

(10) Patent No.: US 8,389,538 B2
(45) Date of Patent: Mar. 5, 2013

(54) REXINOID COMPOUND HAVING ALKOXY GROUP

(75) Inventors: Hiroki Kakuta, Okayama (JP); Kenji Sasaki, Okayama (JP); Kayo Takamatsu, Okayama (JP); Atsushi Takano, Okayama (JP); Nobumasa Yakushiji, Okayama (JP); Kazunori Morohashi, Okayama (JP); Kenichi Morishita, Okayama (JP)

(73) Assignee: National University Corporation Okayama University, Okayama (JP)

( * ) Notice: Subject to any disclaimer, the term of this patent is extended or adjusted under 35 U.S.C. 154(b) by 206 days.

(21) Appl. No.: 12/528,787

(22) PCT Filed: Feb. 26, 2008

(86) PCT No.: PCT/JP2008/053240
§ 371 (c)(1),
(2), (4) Date: Jan. 15, 2010

(87) PCT Pub. No.: WO2008/105386
PCT Pub. Date: Sep. 4, 2008

(65) Prior Publication Data
US 2010/0120742 A1    May 13, 2010

(30) Foreign Application Priority Data

Feb. 27, 2007   (JP) .................................. 2007-048059
Sep. 25, 2007   (JP) .................................. 2007-246591

(51) Int. Cl.
*A01N 43/40* (2006.01)
*A61K 31/435* (2006.01)
*C07D 239/00* (2006.01)
(52) U.S. Cl. ........................................ 514/277; 546/255
(58) Field of Classification Search .................. 546/255; 514/277
See application file for complete search history.

(56) References Cited

U.S. PATENT DOCUMENTS

| 5,962,508 | A | 10/1999 | Billoni et al. | |
|---|---|---|---|---|
| 7,125,880 | B1 * | 10/2006 | Chen | 514/258.1 |
| 2004/0152902 | A1 | 8/2004 | Schumacher et al. | |
| 2005/0119225 | A1 | 6/2005 | Schumacher et al. | |
| 2005/0222207 | A1 * | 10/2005 | Schumacher et al. | 514/318 |
| 2007/0049611 | A1 * | 3/2007 | Talamas et al. | 514/275 |

FOREIGN PATENT DOCUMENTS

| EP | 1180520 A1 | 2/2002 |
|---|---|---|
| JP | 10-338658 A | 12/1998 |
| JP | 2000-159751 A | 6/2000 |
| JP | 2004-250400 A | 9/2004 |
| JP | 2006-504656 A | 2/2006 |
| JP | 2006-508987 A | 3/2006 |
| WO | 00/66595 A1 | 11/2000 |

OTHER PUBLICATIONS

Misbahi et al., Improvement of the Ullmann condensation method for the synthesis of 2-anilinonicotinic acids. Heterocyclic Communications (2003), 9(4), 335-336.*
Ouyang et al., Synthesis and structure-activity relationships of 1,2,4-triazoles as a novel class of potent tubulin polymerization inhibitors. Bioorganic & Medicinal Chemistry Letters (2005), 15(23), 5154-5159.*
Takamatsu, K. et al.: "The first potent subtype-selective retinoid X receptor (RXR) agonist possessing a 3-isopropoxy-4-isopropylphenylamino moiety, NEt-3IP (RXR.alpa./.beta.-dual agonist)" Chem Med Chem, Feb. 22, 2008, pp. 780-787, XP002574626* tables 1,2: compounds 7,8*.
Takahashi, B. et al.: Novel retinoid X receptor antagonists: specific inhibition of retinoid synergism in RXR-RAR heterodimer actions.; J. Med. Chem., vol. 45, No. 16, Aug. 1, 2002, pp. 3327-3330, XP002574627 * abstract; compounds 6a, 6b*.
Hao-Yang Wang et al.,"Mass Spectrometric Studies of the Gas Phase Retro-*Michael* Type Fragmentation Reactions of 2-Hydroxybenzyl-*N*-Pyrimidinylamine Derivatives," Journal of the American Society for Mass Spectrometry, 2005, pp. 1561-1573, vol. 16.
Hao-Yang Wang et al., "Interesting Acid-Catalyzed O—N-Type Smiles Rearrangement Reactions of 2-Pyrimidinyloxy-*N*-Arylbenzylamine Derivatives", Synlett, 2005, pp. 1239-1242, No. 8.
Alexander Mata de Uriquiza, et al., Docosahexaenoic Acid, a Ligand for the Retinoid X Receptor in Mouse Brain, Science, 2000, pp. 2139-2144, vol. 290.
David J. Mangelsdorf et al., "The RXR Heterodimers and Orphan Receptors", Cell, 1995, pp. 841-850. vol. 83.

(Continued)

*Primary Examiner* — Paul V. Ward
(74) *Attorney, Agent, or Firm* — Sughrue Mion, PLLC

(57) ABSTRACT

Disclosed is a compound represented by the general formula shown below, which can bind to a retinoid X receptor (RXR), which is one of nuclear receptors, and exhibit an agonistic or antagonistic action. [Wherein, $R^1$ is selected from the group consisting of an alkyl group, an alkenyl group, an alkynyl group and an aryl group. $R^2$ is selected from the group consisting of an alkoxy group, an alkyl group, an alkenyl group, an alkynyl group and an aryl group. W is $NR^3$ or $CR^3$; and $R^3$ is selected from a hydrogen, an alkyl group, an alkenyl group, an alkynyl group and an aryl group. $X^1$ and $Y^1$ are selected from CH or N. $X^2$ and $Y^2$ are selected from CH, $CR^4$ or N. $R^4$ is selected from an alkyl group, an alkenyl group, an alkynyl group, an alkoxy group, a halogen, a nitro group and an amino group. Z is selected from a carboxylic acid, a carboxylate ester or a hydroxamic acid, which is bound directly or via an alkyl group, an alkenyl group or an alkynyl group.]

Formula (I)

17 Claims, 8 Drawing Sheets

OTHER PUBLICATIONS

"Definition of tamibarotene", NCI Drug Dictionary, http://www.cancer.gov/Templates/drugdictionary.aspx.

Laurence Eyrolles et al., "Retinobenzoic Acids 6 Retinoid Antagonists with a Heterocyclic Ring", J. Med. Chem., 1994, pp. 1508-1517, vol. 37.

Toshimasa Yamauchi et al., "Inhibition of RXR and PPAR y ameliorates diet-induced obesity and type 2 diabetes", The Journal of Clinical Investigation, 2001, pp. 1001-1013, vol. 108, No. 7.

Eric D. Bischoff et al., "Beyond Tamoxifen: The Retinoid X Receptor-selective Ligand LGD1069 (Targretin) Causes Complete Regression of Mammary Carcinoma", Cancer Research, 1998, pp. 479-484, vol. 58.

Clinton J. Grubbs et al., "9cUAB30, an RXR specific retinoid, and/or tamoxifen in the prevention of methylnitrosourea-induced mammary cancers", Cancer Letters, 2003, pp. 17-24, vol. 201.

Wan Ching Yen et. al, "A Selective Retinoid X Receptor Agonist Bexarotene (Targretin) Prevents and Overcomes Acquired Paclitaxel (Taxol) Resistance in Human Non-Small Cell Lung Cancer", Clinical Cancer Research, 2004, pp. 8656-8664, vol. 10.

W-C Yen et al., "A selective retinoid X receptor agonist bexarotene (LGD1069,targretin) inhibits angiogenesis and metastasis i solid tumours", British Journal of Cancer, 2006, vol. 94, pp. 654-660.

Ranjan Mukherjee et al., "Sensitization of diabetic and obese mice to insulin by retinoid X receptor agonists", Nature, 1997, vol. 386, pp. 407-410.

Hiroyuki Kagechika et al., "Synthetic Retinoids: Recent Developments Concerning Structure and Clinical Utility", Journal of Medicinal Chemistry, 2005, pp. 5875-5883, vol. 48, No. 19.

Marcia I. Dawson et. al, "Conformational Effects on Retinoid Receptor Selectivity. 2. Effects of Retinoid Bridging Group on Retinoid X Receptor Activity and Selectivity", J. Med. Chem., 1995, pp. 3368-3383, vol. 38.

Marcus F. Boehm et al., "Synthesis and Structure-Activity Relationships of Novel Retinoid X Receptor-Selective Retinoids", J. Med. Chem., 1994, pp. 2930-2941, vol. 37.

David J. Mangelsdorf et al., "The Nuclear Receptor Superfamily: The Second Decade", Cell, 1995, pp. 835-839, vol. 83.

Scott M. Lippman et al., "Symposium: Diet, Natural Products and Cancer Prevention: Progress and Promise", The Journal of Nutrition Supplement, 2000, pp. 479S-482S.

Kiminori Ohta et al., "Retinoidal Pyrimidinecarboxylic Acids. Unexpected Diaza-Substituent Effects in Retinobenzoic Acids", Chem. Pharm. Bull., 2000, pp. 1504-1513, vol. 48, No. 10.

Stacie S. Canan Koch et al., "Synthesis of Retinoid X Receptor-Specific Ligands That Are Potent Inducers of Adipogenesis in 3T3-L1 Cells", J. Med. Chem., pp. 742-750, vol. 42.

* cited by examiner

REXINOID COMPOUND HAVING ALKOXY GROUP

TECHNICAL FIELD

The present invention relates to a novel compound that acts as an agonist or antagonist to retinoid X receptor (RXR), which is a nuclear receptor, and has an alkoxy group (hereinafter referred to as "rexinoid compound"). The present invention further relates to its action.

The present invention claims priority from Japanese Patent Application Nos. 2007-048059 and 2007-246591, the content of which is incorporated herein by reference.

BACKGROUND ART

Retinoid X receptor (hereinafter abbreviated as "RXR") is one of nuclear receptors, which are ligand-dependent transcription factors, and is believed to make 9-cis retinoic acid and docosahexaenoic acid (DHA) into endogenous ligands. Its function is exerted as a homodimer or a heterodimer formed with various nuclear receptors (Nonpatent document No. 1).

As a heterodimer partner of RXR, in addition to retinoic acid receptor (RAR) involved in cell differentiation and proliferation, vitamin D receptor (VDR) likewise involved in cell differentiation and proliferation and also bone metabolism, peroxisome proliferator-activated receptor (PPAR) involved in lipid metabolism and thyroid hormone receptor (TR), there is PXR associated with the expression of CYP3A4, which is known as a drug-metabolizing enzyme. Therefore, as the function of RXR is closely connected to the active expression of these nuclear receptors, the agonists or antagonists which control the function of RXR can control the functions of these heterodimers (Nonpatent document No. 2).

For example, while RAR agonist Am80 (generic name: tamibarotene; an therapeutic agent for recurrent or intractable acute promyelocytic leukemia: 4-[(5,6,7,8-tetrahydro-5,5,8,8-tetramethyl-2-naphthyl) carbamoyl]benzoic acid: Nonpatent document No. 3) shows little cell differentiation-inducing action when present alone at a concentration of $3.3 \times 10^{-10}$ M, the combined use of Am80 and RXR agonist allows the RXR agonist to function as a synergist of Am80, showing a significant differentiation-inducing action (Nonpatent document No. 4). Such synergistic effects exerted on nuclear receptor heterodimers by RXR agonists can be seen not only on RAR but also on VDR, PPAR and the like which form heterodimers with RXR. Namely, with a highly lipid-soluble pharmaceutical molecule which targets such a nuclear receptor, synergistic effects can be obtained even with a low dose of that drug.

Further, RXR antagonist can selectively inhibit the function of a heterodimer containing RXR. For example, RXR antagonist HX531 can improve insulin resistance and obesity by inhibition of the function of PPAR-RXR heterodimer. Therefore, its pharmaceutical application to type II diabetes is expected (Nonpatent document No. 5).

Actions of RXR agonist are not limited to those mediated by a nuclear receptor heterodimer containing RXR. For example, concerning tamoxifen used for treating breast cancer, while its molecular target is estrogen receptor (ER), which does not form a heterodimer with RXR, RXR agonist has been reported to improve the resistance of estrogen-resistant breast cancer (Nonpatent document No. 6). Preventative effect on carcinogenesis has also been reported by RXR agonist alone or in combination with tamoxifen (Nonpatent document No. 7). Further, effects of RXR agonist on Taxol-resistant cancer has been reported (Nonpatent document No. 8). In addition, the action of RXR agonist to inhibit angiogenesis has also been reported (Nonpatent document No. 9).

Further, the administration of RXR agonist alone even shows an interesting physiological activity. For example, when RXR agonist is administered to mouse models of type II diabetes, the improved insulin resistance and the reduced blood glucose level has been reported (Nonpatent document No. 10).

Further, RXR agonist acts on hair-root cycle to show hair growing effect, and thus its application as a hair restorer has also been reported (Patent document No. 1).

RXR agonists and antagonists are generally referred to as rexinoid. Conventionally developed rexinoid compounds are often highly lipid-soluble (log P>7), so that there remains an anxiety that teratogenicity could be caused by its accumulation in body or its passage through placental barrier. Generally, rexinoid is a compound having in its partial structure a hydrophobic site characterized by a tetramethyltetrahydronaphthyl group as represented by the general formula III and an acidic site consisting of benzoic acid and like (Nonpatent document Nos. 11 and 12, patent document No. 2). For example, compound LGD1069, wherein X is C=$CH_2$; R is a methyl group; and Y and Z are CH, has been known (Nonpatent document No. 13), but they are all highly lipid-soluble.

It has been known that RXR has three subtypes (α, β and γ) (Nonpatent document No. 14). However, ligands selective for those subtypes have not been synthesized to date (Nonpatent document No. 15).

General formula IV:
[Compound 4]

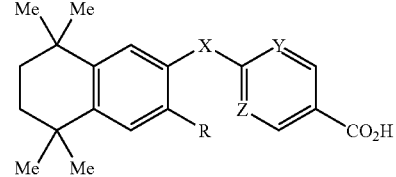

Formula (IV)

Non-patent document No. 1: Science, 290, pp. 2140-2144, 2000
Non-patent document No. 2: Cell, 83, pp. 841-850, 1995
Non-patent document No. 3: Amnolake Tablet 2 mg, Tamibarotene Formulation, NIPPON SHINYAKU CO., LTD. Package insert (Made in June, 2005)
Non-patent document No. 4: Journal of Medicinal Chemistry, 37, pp. 1508-1517, 1994
Non-patent document No. 5: The Journal of Clinical Investigation, 108, pp. 1001-1013, 2001
Non-patent document No. 6: For example, Cancer Research, 58, pp. 479-484, 1998
Non-patent document No. 7: Cancer Letters, 201, pp. 17-24, 2003
Non-patent document No. 8: Clinical Cancer Research, 10, pp. 8656-8664, 2004
Non-patent document No. 9: British Journal of Cancer, 94, pp. 654-660, 2006
Non-patent document No. 10: Nature, 386, pp. 407-410, 1997
Non-patent document No. 11: Journal of Medicinal Chemistry, 48, pp. 5875-5882, 2005
Non-patent document No. 12: Journal of Medicinal Chemistry, 38, pp. 3368-3383, 1995
Non-patent document No. 13: Journal of Medicinal Chemistry, 37, pp. 2930-2941, 1994

Non-patent document No. 14: Cell, 83, pp. 835-839, 1995
Non-patent document No. 15: The Journal of Nutrition, 130, pp. 479S-482S, 2000
Non-patent document No. 16: Chemistry & Pharmaceutical Bulletin, 48, pp. 1504-1513, 2000
Non-patent document No. 17: Journal of Medicinal Chemistry, 42, pp. 742-750, 1999
Patent document No. 1: U.S. Pat. No. 5,962,508-A
Patent document No. 2: Pamphlet of International Patent Publication WO00/66595 (Heterocyclic Carboxylic Acid Derivatives)
Patent document No. 3: Japanese Patent Publication No. JP 10-338658 A (Retinoid Action Regulator)

DISCLOSURE OF THE INVENTION

Problems to be solved by the Invention

The subject of the present invention is to provide a novel compound having a transcriptional regulatory action mainly based on rexinoid action. More specifically, the subject is to provide a novel and safer rexinoid compound with decreased lipid-solublity.

Means to solve the problems

Therefore, the present inventors have strenuously studied to solve the matters described above by converting a hydrophobic site characterized by a tetramethyltetrahydronaphthyl group, which is a structural feature of known rexinoid compounds, to an aromatic ring having a polar alkoxy group, and as a result have found a novel compound with sufficient rexinoid activity while having lower lipid-solublity than existing rexinoid compounds.

Therefore, the present invention consists of the following.
1. A compound represented by the general formula I shown below.

General formula I:
[Compound 1]

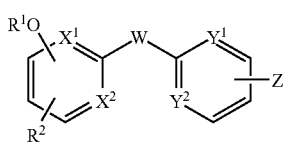

Formula (I)

[wherein,
$R^1$ is selected from the group consisting of straight or branched, unsubstituted or substituted, saturated or unsaturated alkyl, alkenyl, alkynyl and aryl groups,
$R^2$ is selected from the group consisting of straight or branched, unsubstituted or substituted, saturated or unsaturated alkoxy, alkyl, alkenyl, alkynyl and aryl groups,
W is $NR^3$ or $CR^3R^{3'}$, and $R^3$ and $R^{3'}$ are selected from a hydrogen, straight or branched, unsubstituted or substituted, saturated or unsaturated alkyl, alkenyl, alkynyl and aryl groups,
$X^1$ and $Y^1$ are selected from CH or N,
$X^2$ and $Y^2$ are selected from CH, $CR^4$ or N,
$R^4$ is selected from straight or branched, unsubstituted or substituted, saturated or unsaturated alkyl, alkenyl, alkynyl, alkoxy groups, a halogen, a nitro group and an amino group, and Z is selected from a carboxylic acid, a carboxylate ester or a hydroxamic acid, which is bound directly or via a saturated or unsaturated alkyl, alkenyl or alkynyl group.]
2. A compound represented by the general formula II shown below.

General formula II:
[Compound 2]

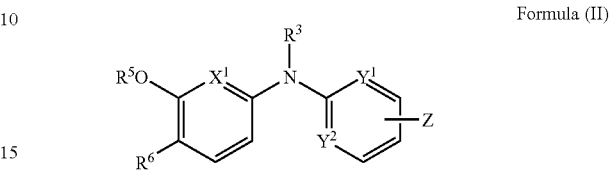

Formula (II)

[wherein,
$R^5$ is selected from the group consisting of straight or branched, unsubstituted or substituted, saturated or unsaturated alkyl, alkenyl, alkynyl and aryl groups,
$R^6$ is selected from the group consisting of branched, unsubstituted or substituted, saturated or unsaturated alkyl and alkenyl groups,
$R^3$ is selected from hydrogen, straight or branched, unsubstituted or substituted, saturated or unsaturated alkyl, alkenyl, alkynyl and aryl groups,
$X^1$ is selected from CH or N,
$Y^1$ is selected from CH or N,
$Y^2$ is selected from CH, $CR^7$ or N,
$R^7$ is selected from straight or branched, unsubstituted or substituted, saturated or unsaturated alkyl, alkenyl, alkynyl and alkoxy groups, and
Z is selected from a carboxylic acid, a carboxylate ester or a hydroxamic acid, which is bound directly or via a saturated or unsaturated alkyl, alkenyl or alkynyl group.]
3. A compound represented by the general formula III shown below.

General formula III:
[Compound 3]

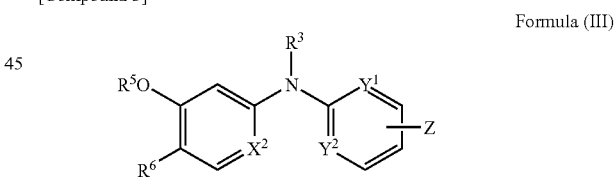

Formula (III)

[wherein,
$R^5$ is selected from the group consisting of straight or branched, unsubstituted or substituted, saturated or unsaturated alkyl, alkenyl, alkynyl and aryl groups,
$R^6$ is selected from the group consisting of a branched, unsubstituted or substituted, saturated or unsaturated alkyl group and alkenyl group,
$R^3$ is selected from a hydrogen, straight or branched, unsubstituted or substituted, saturated or unsaturated alkyl, alkenyl, alkynyl and aryl groups,
$X^2$ is selected from CH, $CR^4$ or N,
$R^4$ is selected from straight or branched, unsubstituted or substituted, saturated or unsaturated alkyl, alkenyl, alkynyl, alkoxy groups, a halogen, a nitro group and an amino group,
$Y^1$ is selected from CH or N,
$Y^2$ is selected from CH, $CR^7$ or N, $R^7$ is selected from straight or branched, unsubstituted or substituted, saturated or unsaturated alkyl, alkenyl, alkynyl and alkoxy groups, and Z is selected from a carboxylic acid, a carboxylate ester or a hydroxamic acid, which is bound directly or via a saturated or unsaturated alkyl, alkenyl or alkynyl group.]

4. A compound according to the preceding aspect 2 or 3, wherein in the general formula II or III, $R^5$ and $R^6$ are both isopropyl groups; $X^1$ is CH or N; $X^2$ is CH, $CR^4$ or N; $Y^1$ and $Y^2$ are both N; Z is a carboxylate ester, a carboxylic acid or salts thereof and located in meta position to $Y^1$ and $Y^2$; and $R^3$ is selected from an ethyl group and an isopropyl group.

5. A compound according to the preceding aspect 2 or 3, wherein in the general formula II or III, $R^5$ is an isopropyl group or an isobutyl group; $X^1$ is CH or N; $X^2$ is CH, $CR^4$ or N; $R^6$ is an isopropyl group; $X^1$ is CH or N; $Y^1$ is CH or N; $Y^2$ is CH or N; Z is a carboxylate ester, a carboxylic acid or salts thereof and located in meta position to $Y^1$ and $Y^2$; and $R^3$ is an ethyl group.

6. A compound according to the preceding aspect 2 or 3, wherein in the general formula II or III, $R^5$ is an isopropyl or an isobutyl group; $R^6$ is an isopropyl group; $X^1$ is CH; $X^2$ is CH, $CR^4$ or N; $Y^1$ is N; $Y^2$ is CH; Z is a carboxylic acid and located in meta position to $Y^1$ and $Y^2$; and $R^3$ is an ethyl group.

7. A compound according to the preceding aspect 2 or 3, wherein in the general formula II or III, $R^5$ is an isopropyl group; $R^6$ is an isopropyl group; $X^1$ is CH; $X^2$ is CH, $CR^4$ or N; $Y^1$ is N; $Y^2$ is CH; Z is a hydroxamic acid or an acrylhydroxamic acid and is located in meta position to $Y^1$ and $Y^2$; and $R^3$ is an ethyl group.

8. An agent comprising a compound according to any one of the preceding aspects 1 to 7 as an active ingredient.

9. An agent according to the preceding aspect 8, wherein the agent is an anticancer and/or anti-inflammatory agent.

10. An agent according to the preceding aspect 8 or 9, wherein the active ingredient is a transcription regulator and nuclear receptor ligand action regulator.

11. An agent according to the preceding aspect 8 or 10, further comprising an anticancer agent as an active ingredient.

12. An agent according to the preceding aspect 8 or 10, further comprising an anti-inflammatory agent as an active ingredient.

13. A pharmaceutical composition comprising an agent according to any one of the preceding aspects 8 to 12 and a pharmacologically and pharmaceutically acceptable carrier.

EFFECTS OF INVENTION

When acted together with tamibarotene (Am80), which is an existing compound for regulating the induction of cell differentiation, the compound of the present invention exhibited a significant retinoid synergistic activity through RXR agonistic effects. Further, a compound additionally having an inhibitory activity against histone deacetylase (HDAC) was found.

DESCRIPTION OF THE PREFERRED EMBODIMENT

Figure 1:
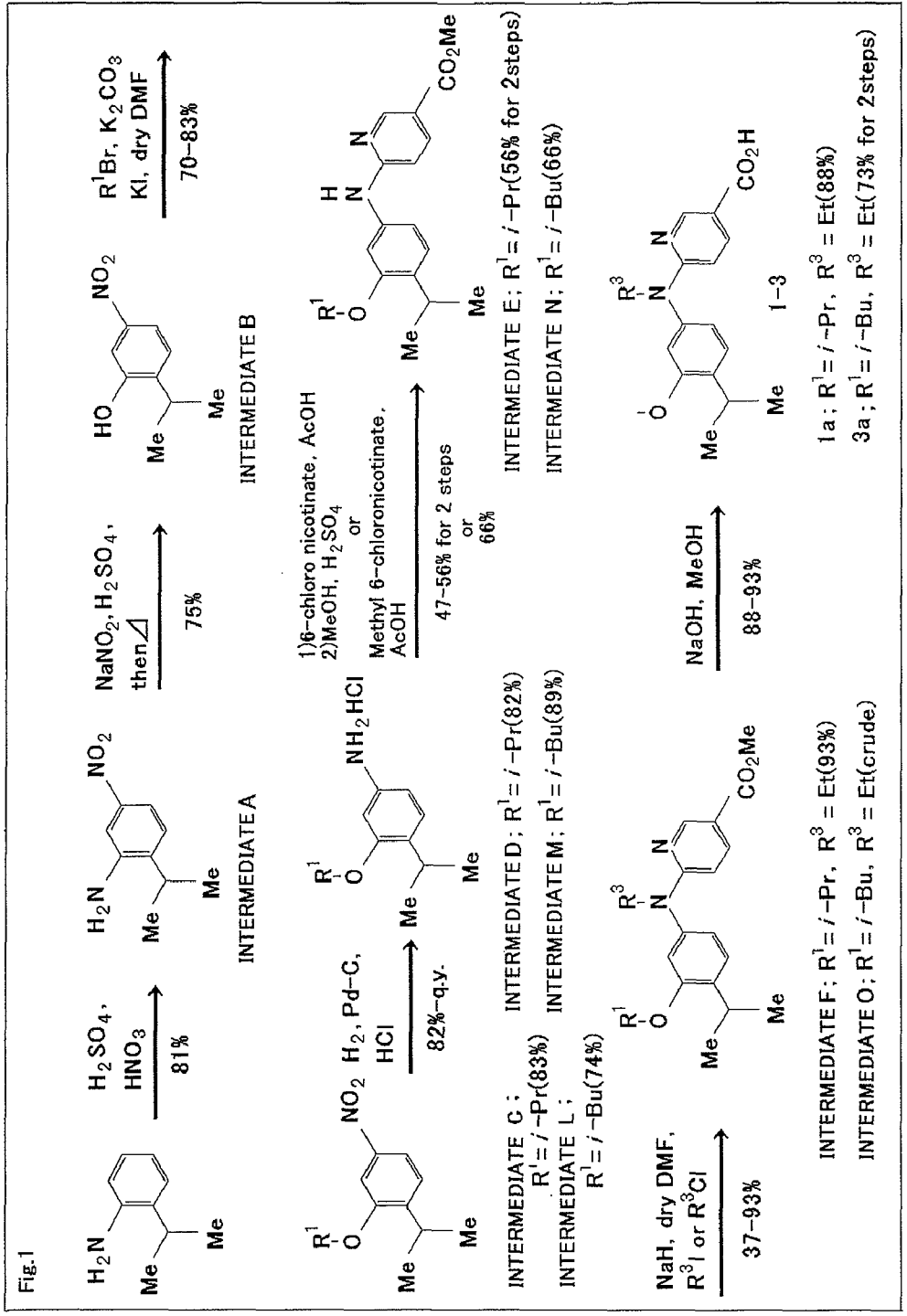
FIG. 1 shows the synthetic scheme of compounds of Examples 1 and 4

The compound of the present invention is represented by the general formula I shown below.

General formula I:

[Compound 1]

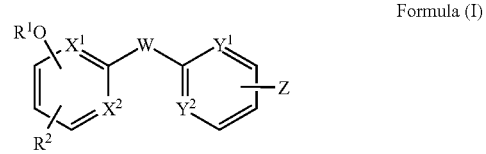

Formula (I)

[wherein, $R^1$ is selected from the group consisting of straight or branched, unsubstituted or substituted, saturated or unsaturated alkyl, alkenyl, alkynyl and aryl groups, $R^2$ is selected from the group consisting of straight or branched, unsubstituted or substituted, saturated or unsaturated alkoxy, alkyl, alkenyl, alkynyl and aryl groups, W is $NR^3$ or $CR^3R^{3'}$, and $R^3$ and $R^{3'}$ are selected from a hydrogen, straight or branched, unsubstituted or substituted, saturated or unsaturated alkyl, alkenyl, alkynyl and aryl groups, $X^1$ and $Y^1$ are selected from CH or N, $X^2$ and $Y^2$ are selected from CH, $CR^4$ or N, $R^4$ is selected from straight or branched, unsubstituted or substituted, saturated or unsaturated alkyl, alkenyl, alkynyl, alkoxy groups, a halogen, a nitro group and an amino group, and Z is selected from a carboxylic acid, a carboxylate ester or a hydroxamic acid, which is bound directly or via a saturated or unsaturated alkyl, alkenyl or alkynyl group.]

Of compounds represented by the general formula I, those represented by the general formula II or III shown below are preferred.

General formula II:

[Compound 2]

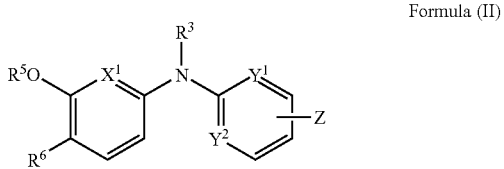

Formula (II)

[wherein, $R^5$ is selected from the group consisting of straight or branched, unsubstituted or substituted, saturated or unsaturated alkyl, alkenyl, alkynyl and aryl groups, R[6] is selected from the group consisting of branched, unsubstituted or substituted, saturated or unsaturated alkyl and alkenyl groups, R[3] is selected from hydrogen, straight or branched, unsubstituted or substituted, saturated or unsaturated alkyl, alkenyl, alkynyl and aryl groups, X[1] is selected from CH or N, Y[1] is selected from CH or N, Y[2] is selected from CH, CR[7] or N, R[7] is selected from straight or branched, unsubstituted or substituted, saturated or unsaturated alkyl, alkenyl, alkynyl and alkoxy groups, and Z is selected from a carboxylic acid, a carboxylate ester or a hydroxamic acid, which is bound directly or via a saturated or unsaturated alkyl, alkenyl or alkynyl group.]

General formula III:
[Compound 3]

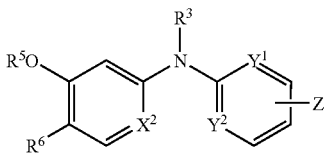

Formula (III)

[wherein,

R[5] is selected from the group consisting of straight or branched, unsubstituted or substituted, saturated or unsaturated alkyl, alkenyl, alkynyl and aryl groups, R[6] is selected from the group consisting of branched, unsubstituted or substituted, saturated or unsaturated alkyl and alkenyl groups, R[3] is selected from a hydrogen, straight or branched, unsubstituted or substituted, saturated or unsaturated alkyl, alkenyl, alkynyl and aryl groups, X[2] is selected from CH, CR[4] or N, R[4] is selected from straight or branched, unsubstituted or substituted, saturated or unsaturated alkyl, alkenyl, alkynyl, alkoxy groups, a halogen, a nitro group and an amino group, Y[1] is selected from CH or N, Y[2] is selected from CH, CR[7] or N, R[7] is selected from straight or branched, unsubstituted or substituted, saturated or unsaturated alkyl, alkenyl, alkynyl and alkoxy groups, and Z is selected from a carboxylic acid, a carboxylate ester or a hydroxamic acid, which is bound directly or via a saturated or unsaturated alkyl, alkenyl or alkynyl group.]

In the general formulae I to III, alkyl group, alkenyl group and alkynyl group may each be cycloalkyl group, cycloalkenyl group and cycloalkynyl group respectively. Cycloalkyl used herein means a saturated cyclic carbon chain, and cycloalkenyl and cycloalkynyl means cyclic carbon chain containing at least one double or triple bond respectively. Cycloalkyl group, cycloalkenyl group, cycloalkynyl group and aryl group may be a monocyclic, a polycyclic or a condensed cyclic group.

Examples of the preferred compound of the present invention include the following.

Compounds represented by the general formula II, wherein R[5] and R[6] are both isopropyl groups; X[1] is CH or N; Y[1] and Y[2] are both N; Z is a carboxylate ester, a carboxylic acid or salts thereof and located in meta position to Y[1] and Y[2]; and R[3] is selected from an ethyl group and an isopropyl group may be included. Examples of carboxylate ester include a methyl ester, an ethyl ester and a t-butyl ester. More specifically, compounds represented by the formula V below may be included.

Other preferred compounds of the present invention include the following.

Compounds represented by the general formula III, wherein R[5] and R[6] are both isopropyl groups; X[2] is CH; Y[1] is N; Y[2] is CH; Z is a carboxylate ester, a carboxylic acid or salts thereof and is located in meta position to Y[1] and Y[2]; and R[3] is selected from an ethyl group and an isopropyl group, may be included. Examples of carboxylate ester include a methyl ester, an ethyl ester and a t-butyl ester. More specifically, compounds represented by the formula VI below may be included.

Other preferred compounds of the present invention include the following.

Compounds represented by the general formula II, wherein R[5] is an isopropyl group or an isobutyl group; R[6] is an isopropyl group; X[1] is CH or N; Y[1] is CH or N; Y[2] is N; Z is a carboxylate ester, a carboxylic acid or salts thereof and located in meta position to Y[1] and Y[2]; and R[3] is an ethyl group, may be included. Examples of carboxylate ester include a methyl ester, an ethyl ester and a t-butyl ester. More specifically, compounds represented by the general formula VII and shown in Table 1 may be included.

Formula V:
[Compound 5]

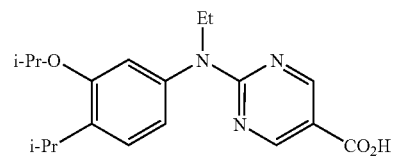

Formula (V)

Formula VI:
[Compound 6]

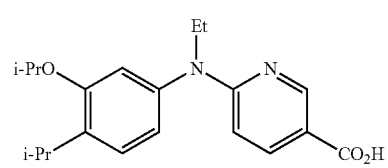

Formula (IV)

Formula VII:
[Compound 7]

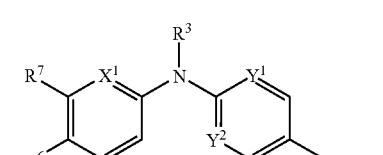

Formula (VII)

TABLE 1

| Compound | R[7] | R[6] | R[3] | X[1] | Y[1] | Y[2] |
|---|---|---|---|---|---|---|
| 1a (NEt-3IP) | O-i-Pr | i-Pr | Et | CH | N | CH |
| 1b | O-i-Pr | i-Pr | Ms | CH | N | CH |
| 1c | O-i-Pr | i-Pr | H | CH | N | CH |
| 2a | O-n-Pr | i-Pr | Et | CH | N | CH |
| 2b | O-n-Pr | i-Pr | Ms | CH | N | CH |
| 2c | O-n-Pr | i-Pr | H | CH | N | CH |
| 3a (NEt-3IB) | O-i-Bu | i-Pr | Et | CH | N | CH |
| 4a (NEt-4IP) | i-Pr | O-i-Pr | Et | CH | N | CH |
| 4c | i-Pr | O-i-Pr | H | CH | N | CH |
| 5c | i-Pr | O-n-Pr | H | CH | N | CH |
| 6a (PEt-3IP) | O-i-Pr | i-Pr | Et | CH | N | N |
| 7a (PEt-3IB) | O-i-Bu | i-Pr | Et | CH | N | N |
| A | O-i-Pr | i-Pr | i-Pr | CH | N | N |
| B | O-i-Pr | i-Pr | Et | N | N | N |
| C | O-i-Pr | i-Pr | Et | N | N | CH |

In the present invention, compounds represented by any of the general formulae I to III may also be their pharmacologically acceptable salts. Further, if the compounds of the general formula I or the salts thereof have their isomers (for example, optical isomer, geometric isomer and tautomer), the present invention comprises those isomers and also their solvates, hydrates, and crystals in various forms.

Pharmaceutically acceptable salts in the present invention may include general pharmacologically and pharmaceutically acceptable salts. Examples of such salts are as follows.

Basic addition salts include, for example, alkali metal salts such as sodium salts and potassium salts; alkaline-earth metal salts such as calcium salts and magnesium salts; ammonium salts; trimethylamine salts and triethylamine salts; aliphatic amine salts such as dicyclohexylamine salts, ethanolamine salts, diethanolamine salts, triethanolamine salts and brocaine salts; aralkylamine salts such as N,N-dibenzylethylenediamine; heterocyclic aromatic amine salts such as pyridine salts, picoline salts, quinoline salts and isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts and tetrabutylammonium salts; arginine salts; and basic amino acid salts such as lysine salts.

Acid addition salts include, for example, inorganic acids such as hydrochlorides, sulfates, nitrates, phosphates, carbonates, bicarbonates, and perchlorates; organic acid salts such as acetates, propionates, lactates, maleates, fumarates, tartrates, malates, citrates and ascorbates; sulfonates such as methanesulfonates, isethionates, benzenesulfonates and p-toluenesulfonates; and acidic amino acids such as aspartates and glutamates.

In the present invention, a compound represented by any of the general formulae I to III has agonistic or antagonistic action on RXR. Since RXR is a nuclear receptor associated with DNA transcription, the compound of the present invention can be referred to as a transcription-regulating compound. The term "Regulatory action" or the synonyms thereof herein should be construed in the broadest sense, including the enhancement or inhibition of the action. Which action, enhancing one or inhibiting one, the compound of the present invention has, can be easily assayed according to the methods specifically described in Experimental Examples herein.

In the present invention, of compounds represented by any of the general formulae I to III, RXR agonist has a synergistic action which significantly enhances physiological actions such as actions of cell differentiation and cell inhibition of retinoid. Therefore, the compounds can be used as an action enhancer in the treatment by using a pharmaceutical composition comprising retinoid, which includes retinoic acid and compounds having a retinoic acid-like biological activity (for example, Am80). Representative biological activities of retinoid include the actions of cell differentiation, cell inhibition and life-support. Further, retinoid is considered to be useful for treating and preventing vitamin A deficiency, cornification of epithelial tissues, rheumatism, delayed allergy, bone disease, leukemia and certain cancers. Further, even in the case of not administering retinoid, the compound of the present invention itself can be administered because it can enhance the action of retinoic acid already present in the body.

The compound described above can enhance or inhibit the actions of substances which bind to receptors belonging to the superfamily of nuclear receptors present in the nucleus of a cell and express biological activity, for example, retinoid compounds including an active form of vitamin A metabolite (All-trans Retinoic Acid: ATRA); eicosanoids; vitamin D compounds such as vitamin D3; or thyroxine or orphan receptor ligands in which ligands are unknown.

Further, of the compounds of the present invention, compounds having an RXR antagonistic action can be used as a retinoid action inhibitor. Therefore, namely, they can inhibit the actions of substances which can bind to receptors belonging to the superfamily of nuclear receptors present in the nucleus of a cell and express biological activity, for example, retinoid compounds including ATRA; eicosanoids, vitamin D compounds such as vitamin D3; or thyroxine or orphan receptor ligands in which ligands are unknown.

Therefore, RXR agonistic or inhibitory compounds can be used for regulating the expression of actions of these biologically active substances, thereby being used for preventing and/or treating the diseases associated with unusual biological actions in which one or more nuclear receptors belonging to the nuclear receptor superfamily are involved.

In the present invention, compounds represented by the general formulae VIII to XI have, besides RXR agonistic action, an action as a histone deacetylase inhibitor (HDAC). Therefore, in addition to RXR agonistic action, the actions of transcription-activation, cell differentiation and apoptosis, which are based on HDAC inhibition, can be expected.

General formula VIII:

[Compound 8]

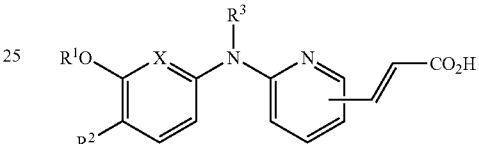

Formula (VIII)

General formula IX:

[Compound 9]

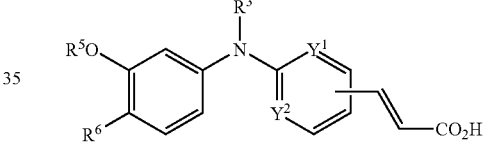

Formula (IX)

General formula X:

[Compound 10]

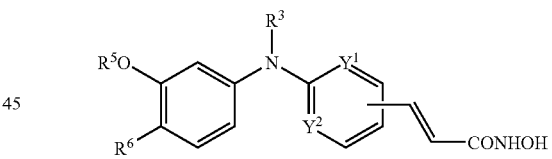

Formula (X)

General formula XI:

[Compound 11]

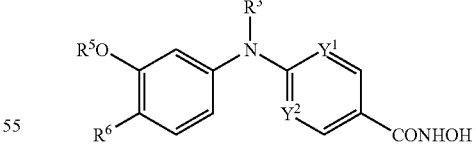

Formula (XI)

Agents such as reagents or pharmaceuticals comprising the compound of the present invention as an active ingredient are also included in the present invention. When used as the pharmaceuticals, they can be used as, for example, anticancer agent, anti-inflammatory agent, anti-metabolic syndrome agent and/or hair grower and hair restorer.

When the compound of the present invention is used as an active ingredient for the pharmaceuticals, the amount of administration is not limited in particular. For example, when the compound of the present invention is used with a pharmaceutical agent comprising retinoid such as retinoic acid as an active ingredient for regulating retinoid action, or when the agent of the present invention is administered without a pharmaceutical agent comprising retinoid in order to regulate the action of retinoic acid already present in the body, the appropriate amount of administration can easily be selected in any administration method. For example, for oral administration, the active ingredient within the range of 0.01 to 1000 mg per day can be used for the adult. When a pharmaceutical agent comprising retinoid as an active ingredient and the agent of the present invention are used at the same time, the agent of the present invention can be administered during and/or before or after the administration of retinoid.

Further, when the agent of the present invention is used as an anticancer agent, in addition to the compound of the present invention described above used as an active ingredient, a well-known anticancer agent may be contained also as an active ingredient. Anticancer agents include estrogen-antagonistic anti-breast cancer agents and taxane-based anticancer agents, specifically such as tamoxifen or Taxol.

When the agent of the present invention is used as an anti-inflammatory agent, in addition to the compound of the present invention described above used as an active ingredient, a well-known anti-inflammatory agent may be contained also as an active ingredient. Anti-inflammatory agents may be either steroidal or non-steroidal. A non-steroidal antiinflammatory agent may be selected from aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazin carboxamides, and those having other structures.

When the agent of the present invention is used as an anti-metabolic syndrome agent, in addition to the compound of the present invention described above used as an active ingredient, a well-known anti-metabolic syndrome agent may be contained also as an active ingredient.

Metabolic syndrome is a complexed risk syndrome which may increase the risk of atherosclerotic diseases (for example, myocardial infarction and cerebral infarction) characterized by exhibiting two or more of the following: (1) abnormal serum lipid (triglyceride value of 150 mg/dL or more, or HDL cholesterol value of below 40 mg/dL), (2) high blood pressure (maximum blood pressure of 130 mmHg or more, or minimum blood pressure of 83 mmHg or more) and (3) hyperglycemia (fasting plasma glucose of 110 mg/dL)). In particular, obesity by visceral fat accumulation is attracting attention as a common risk of hyperlipidemia, hypertension and hyperglycemia.

The fact that the agonist of peroxisome proliferator-activated receptor (PPAR) which is involved in lipid metabolism and known as the partner of RXR heterodimer has antimetabolic action has been revealed and drawing attention by recent studies. The compound of the present invention exhibits synergistic action against PPAR which is RXR heterodimer partner, thereby the antimetabolic syndrome action of PPAR agonist being enhanced.

Though one or more substances selected from compounds represented by the general formula I shown above may be administered as is as the agents of the present invention, preferably they are administered as an oral or parenteral pharmaceutical composition comprising one or more substances indicated above. The oral or parenteral pharmaceutical composition can be produced using formulation additives available for those skilled in the art, namely, pharmacologically and pharmaceutically acceptable carriers. For example, a pharmaceutical composition in the form of so called drug combination can be used by mixing a pharmaceutical agent comprising as an active ingredient retinoid such as retinoic acid with one or more substances indicated above.

As a pharmaceutical composition suitable for oral administration, for example, tablet, capsule, dispersant, fine granule, granule, liquid, and syrup and the like can be included and as a pharmaceutical composition suitable for parenteral administration, for example, injection, infusion, suppository, inhalant, eye drop, nose drop, ointment, cream, adhesive skin patch and the like can be included. Pharmacologically and pharmaceutically acceptable carriers used in the production of the pharmaceutical composition described above include, for example, excipient, disintegrating agent or disintegrating aid, binder, lubricant, coating agent, pigment, diluent, base, solubilizer or solubilizing agent, isotonic agent, pH regulator, stabilizer, propellant, and adhesive can be included.

Methods for producing a preferred compound of the present invention represented by the formula I will specifically be explained in Examples herein. Any compounds within the scope of the present invention can be produced by modifying or changing starting materials, reagents and reaction conditions used in these production methods as appropriate. The methods for producing the compound of the present invention are not limited to those specifically explained in the Examples.

EXAMPLES

The present invention will be explained in more detail below with reference to Examples, but is not limited within the Examples described below.

Example 1

Synthesis of Target Compound 1a (Net-3IP)

The scheme of production method in this Example will be shown in FIG. 1.

1) Synthesis of Intermediate A 2-isopropyl aniline (2.7 g, 20.0 mmol) and concentrated sulfuric acid (5 mL) were mixed under cooling in an ice bath, and then mixed acid (concentrated nitric acid:concentrated sulfuric acid=2:5, 7 mL) was added while not allowing the temperature to increase beyond 0° C. Then, the completion of the reaction was confirmed on TLC (Thin Layer Chromatography) plates (ethyl acetate n-hexane=1:2). After neutralization was performed by using 2 N aqueous sodium hydroxide, the resultant solution was extracted with ethyl acetate (70 mL×3). Organic layer was washed with water (100 mL×2) and saturated saline solution (50 mL). After the obtained organic layer was dried using magnesium sulfate, the solvent was distilled off under reduced pressure to yield dark orange oil of Intermediate A (2.9 g, 81%).

$^1$H NMR (500 MHz, CDCl$_3$) δ 7.60 (dd, 1 H, J=8.5 Hz and 2.5 Hz, Ar—H), 7.50 (d, 1 H, J=2.5 Hz, Ar—H), 7.24 (d, 1 H, J=8.5 Hz, Ar—H), 3.95 (br s, 2 H, NH$_2$), 2.90 (sept, 1 H, J=7.0 Hz, CH(CH$_3$)$_2$), 1.29 (d, 6 H, J=7.0 Hz, CH(CH$_3$)$_2$).

2) Synthesis of Intermediate B

Intermediate A (2.9 g, 16.0 mmol) was mixed with water (20.0 mL) and concentrated sulfuric acid (4.0 mL) under stirring, then cooled to a temperature between 0 and 5° C., and 4.5 M aqueous sodium nitrite (4.0 mL) was added thereto dropwise and stirred, while not allowing the temperature to increase to 5° C. or more. After confirming the degree of reaction progress with potassium iodide-starch papers, the solution was added dropwise to a hot bath (concentrated sulfuric acid:water=4:3, 7 mL) at 120° C. After the completion of the reaction was confirmed on TLC plates (ethyl acetate:n-hexane=1:5), the resultant solution was extracted with ethyl acetate (50 mL×2). Organic layer was washed with water (70 mL×2) and saturated saline solution (50 mL). After the obtained organic layer was dried using magnesium sulfate, the solvent was distilled off under reduced pressure to yield black oil residue (2.7 g). Flash column chromatography (ethyl acetate:n-hexane=1:5) yielded orange oil of Intermediate B (2.2 g, 75%).

$^1$H NMR (500 MHz, CDCl$_3$) δ 7.78 (dd, 1 H, J=8.5 Hz and 2.0 Hz, Ar—H), 7.63 (d, 1 H, J=2.0 Hz, Ar—H), 7.33 (d, 1 H, J=8.5 Hz, Ar—H), 5.35 (s, 1 H, OH), 3.31 (sept, 1 H, J=7.0 Hz, CH(CH$_3$)$_2$), 1.28 (d, 6 H, J=7.0 Hz, CH(CH$_3$)$_2$).

3) Synthesis of Intermediate C

Intermediate B (2.2 g, 12.0 mmol) was dissolved in anhydrous N,N-dimethylformamide (6.0 mL), the resultant solution was mixed with potassium carbonate (3.3 g, 24.0 mmol), 2-bromopropane (1.7 mL, 18.0 mmol) and an appropriate amount of potassium iodide under stirring, and the resultant solution was heated with stirring for 1.5 hours. After the completion of the reaction was confirmed on TLC plates (ethyl acetate: n-hexane=1:10), the solution was poured into water (70 mL) and the resultant solution was extracted with ethyl acetate (50 mL×2). Organic layer was washed using water (50 mL×2) and saturated saline solution (40 mL). After the obtained organic layer was dried using magnesium sulfate, the solvent was distilled off under reduced pressure to yield orange oil crude product (2.3 g). Flash column chromatography (ethyl acetate:n-hexane=1:10) yielded yellow clear oil of Intermediate C (2.2 g, 83%).

$^1$H NMR (500 MHz, CDCl$_3$) δ 7.78 (dd, 1 H, J=8.5 Hz and 2.0 Hz, Ar—H), 7.63 (d, 1 H, J=2.0 Hz, Ar—H), 7.33 (d, 1 H, J=8.5 Hz, Ar—H), 5.35 (s, 1 H, OH), 3.31 (sept, 1 H, J=7.0 Hz, CH(CH$_3$)$_2$), 1.28 (d, 6 H, J=7.0 Hz, CH(CH$_3$)$_2$).

4) Synthesis of Intermediate D

Intermediate C (2.2 g, 10 mmol) was dissolved in methanol (20 mL), then concentrated hydrochloric acid (0.5 mL) and an appropriate amount of palladium carbon were added, and the resultant solution was then stirred for 1.5 hours at room temperature under hydrogen atmosphere. After the completion of the reaction was confirmed on TLC plates (ethyl acetate:n-hexane=1:10), filtration was carried out with celite, and then the solvent was distilled off under reduced pressure to yield light brown plate-like crystal Intermediate D (1.6 g, 82%).

$^1$H NMR (500 MHz, DMSO-d6) δ 9.84 (br s, 2 H, NH$_2$), 7.24 (d, 1 H, J=8.0 Hz, Ar—H), 6.97 (s, 1 H, Ar—H), 6.85 (d, 1 H, J=8.0 Hz, Ar—H), 4.53 (sept, 1 H, J=6.0 Hz, OCH(CH$_3$)$_2$), 3.20 (sept, 1 H, J=7.0 Hz, CH(CH$_3$)$_2$), 1.31 (d, 6 H, J=6.0 Hz, OCH(CH$_3$)$_2$), 1.15 (d, 6 H, J=7.0 Hz, CH(CH$_3$)$_2$).

5) Synthesis of Intermediate E

Intermediate D (4.9 mmol) and 6-chloronicotinic acid (788 mg, 5.0 mmol) were dissolved in acetic acid (4.0 mL), and the resultant solution was heated to 80° C. with stirring for 8 hours. After the completion of the reaction was confirmed on TLC plates (ethyl acetate:n-hexane=1:4), the solvent was distilled off under reduced pressure to yield black oil residue. To the obtained residue, anhydrous methanol (5.0 mL) and concentrated sulfuric acid (0.2 mL) were added under stirring and refluxed for 18 hours at 90° C. After the completion of the reaction was confirmed by TLC (ethyl acetate:n-hexane=1:4), sodium bicarbonate aqueous solution was added to neutralize the solution, and then extraction was carried out with ethyl acetate (50 mL×3). After organic layer was washed with water (50 mL×2) and saturated saline solution (50 mL), the washed layer was then dried using magnesium sulfate. The solvent was distilled off under reduced pressure to yield crude crystal (1.22 g). Flash column chromatography (ethyl acetate: n-hexane=1:10→1:5) yielded purple granular crystal (702 mg). This was further recrystallized (methanol) to yield colorless granular crystal of Intermediate E (393 mg, 56%).

$^1$H NMR (300 MHz, CDCl$_3$) δ 8.75 (d, 1 H, J=2.5 Hz, Ar—H), 8.08 (dd, 1 H, J=9.0 Hz and 2.5 Hz, Ar—H), 7.69 (s, 1 H, NH), 7.19 (d, 1 H, J=8.0 Hz, Ar—H), 6.83 (d, 1 H, J=9.0 Hz, Ar—H), 6.82 (d, 1 H, J=2.0 Hz, Ar—H), 6.81 (dd, 1 H, J=8.0 Hz and 2.0 Hz, Ar—H), 4.51 (sept, 1 H, J=6.0 Hz, OCH(CH$_3$)$_2$), 3.90 (s, 3 H, CO$_2$CH$_3$), 3.32 (sept, 1 H, J=7.0 Hz, CH(CH$_3$)$_2$), 1.35 (d, 6 H, J=6.0 Hz, OCH(CH$_3$)$_2$), 1.21 (d, 6 H, J=7.0 Hz, CH(CH$_3$)$_2$).

6) Synthesis of Intermediate F

After sodium hydride (60%, in oil) (16 mg, 0.40 mmol) was washed with n-hexane, anhydrous N,N-dimethylformamide (1 mL) was added for suspension, then Intermediate E (115 mg, 0.35 mmol) was added thereto, and the resultant solution was stirred for 5 minutes. Then, iodoethane (32 μL, 0.4 mmol) was added and stirred for 15 hours at room temperature. Reaction was followed up on TLC plates (ethyl acetate:n-hexane=1:4). As the progress of reaction was bad, 1-iodoethane (20 μL) was added, and the resultant solution was stirred for another 2 hours. After the completion of the reaction was confirmed on TLC plates (ethyl acetate:n-hexane=1:4), the solution was poured into water (20 mL) and the resultant solution was extracted with ethyl acetate (10 mL×3). After the obtained organic layer was washed with water (10 mL×2) and saturated saline solution (10 mL), the washed layer was then dried using magnesium sulfate. The solvent was distilled off under reduced pressure to yield yellow oil of Intermediate F (117 mg, 93%).

$^1$H NMR (300 MHz, CDCl$_3$) δ 8.84 (d, 1 H, J=2.5 Hz, Ar—H), 7.79 (dd, 1 H, J=9.0 Hz and 2.5 Hz, Ar—H), 7.25 (d, 1 H, J=8.0 Hz, Ar—H), 6.75 (dd, 1 H, J=8.0 Hz and 2.0 Hz, Ar—H), 6.66 (d, 1 H, J=2.0 Hz, Ar—H), 6.25 (d, 1 H, J=9.0 Hz, Ar—H), 4.48 (sept, 1 H, J=6.0, OCH(CH$_3$)$_2$), 4.03 (q, 2 H, J=7.0 Hz, NCH$_2$CH$_3$), 3.86 (s, 3 H, CO$_2$CH$_3$), 3.32 (sept, 1 H, J=7.0 Hz, CH(CH$_3$)$_2$), 1.33 (d, 6 H, J=6.0 Hz, OCH(CH$_3$)$_2$), 1.24 (d, 6 H, J=7.0 Hz, CH(CH$_3$)$_2$), 1.24 (t, 3 H, J=7.0 Hz, NCH$_2$CH$_3$).

7) Synthesis of Target Compound 1a

Intermediate F (116 mg, 0.33 mmol) was dissolved in methanol (2 mL), then 2 N aqueous sodium hydroxide (0.5 mL) was added thereto, and the resultant solution was stirred for 40 minutes on water bath at 60° C. After the completion of the reaction was confirmed on TLC plates (ethyl acetate:n-hexane=1:1), the solution was poured into saturated ammonium chloride aqueous solution (20 mL), and the resultant solution was extracted with ethyl acetate (10 mL×3). After the obtained organic layer was washed with water (10 mL×2) and saturated saline solution (10 mL), the washed layer was then dried using magnesium sulfate. The solvent was distilled off under reduced pressure to yield colorless residue (105 mg, 88%) of the target. Recrystallization (methanol) yielded colorless needle crystal of the target compound 1a (48 mg, 43%).

$^1$H NMR (500 MHz, CDCl$_3$) δ 8.91 (d, 1 H, J=2.5 Hz, Ar—H), 7.83 (dd, 1 H, J=9.0 Hz and 2.5 Hz, Ar—H), 7.26 (d, 1 H, J=8.0 Hz, Ar—H), 6.74 (dd, 1 H, J=8.0 Hz and 2.0 Hz, Ar—H), 6.65 (d, 1 H, J=2.0 Hz, Ar—H), 6.26 (d, 1 H, J=9.0 Hz, Ar—H), 4.49 (sept, 1 H, J=6.0 Hz, OCH(CH$_3$)$_2$), 4.06 (q, 2 H, J=7.0 Hz, NCH$_2$CH$_3$), 3.32 (sept, 1 H, J=7.0 Hz, CHH(CH$_3$)$_2$), 1.34 (d, 6 H, J=6.0 Hz, OCH(CH$_3$)$_2$), 1.25 (d, 6 H, J=7.0 Hz, CH(CH$_3$)$_2$), 1.24 (t, 3 H, J=7.0 Hz, NCH$_2$CH$_3$).

Mp 212.0-214.0° C.

IR (KBr) cm$^{-1}$: 1698 (CO)

FAB-MS m/e: 343 [M+H]$^+$

Anal. Calcd for C$_{20}$H$_{26}$N$_2$O$_3$: C, 70.15; H, 7.65; N, 8.18. Found: C, 70.18; H, 7.71; N, 8.46.

Example 2

Synthesis of Target Compound 6a

Figure 2:
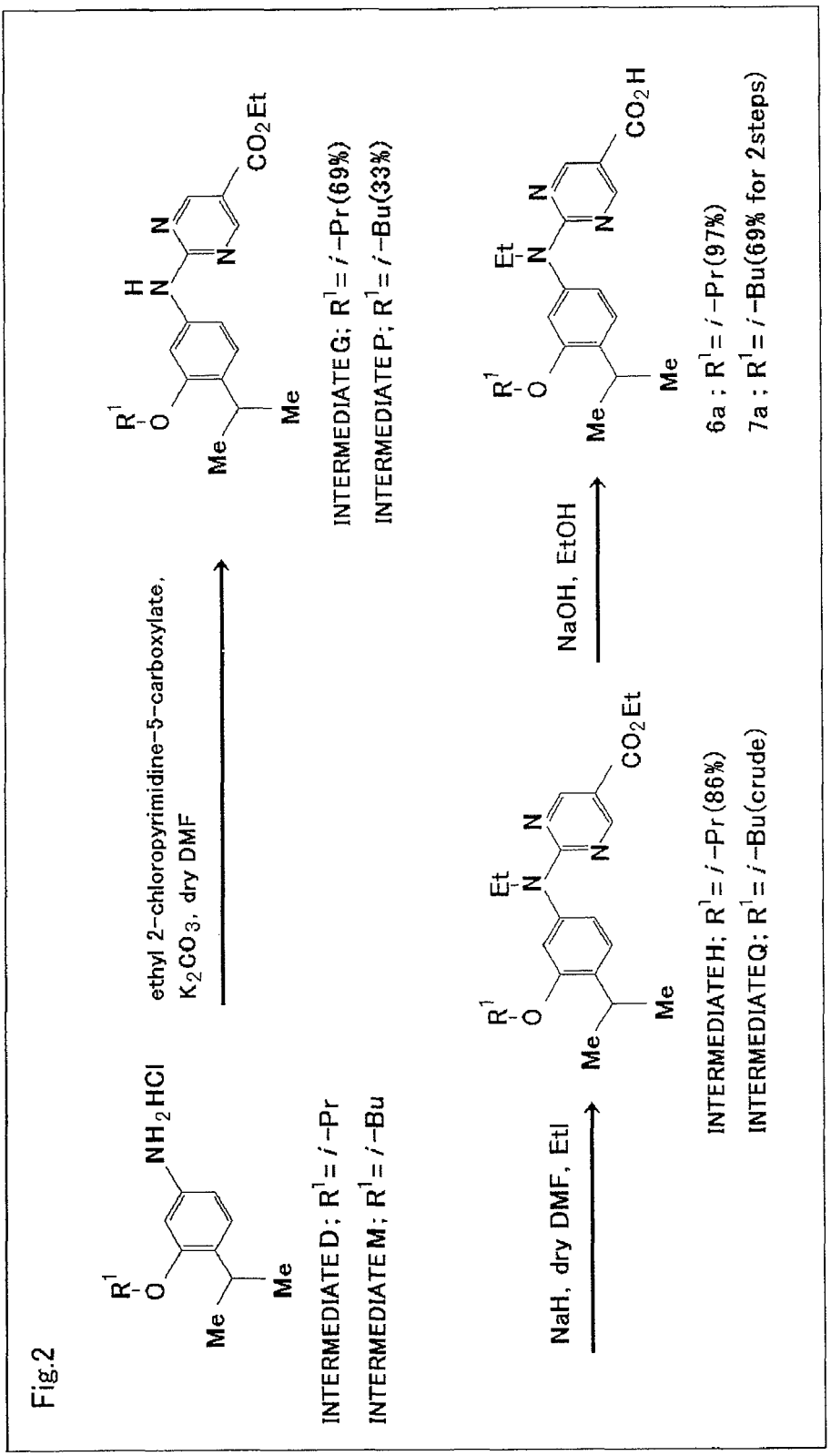
FIG. 2 shows the synthetic scheme of compounds of Examples 2 and 5.

The scheme of production method in this Example will be shown in FIG. 2.

1) Synthesis of Intermediate G

To the mixture of Intermediate D (148 mg, 0.6 mmol), potassium carbonate (622 mg, 4.5 mmol) and 2-chloropyrimidine-5-carboxylic acid ethyl ester (120 mg, 0.6 mmol), a drop of anhydrous N,N-dimethylformamide was added, and the resultant solution was heated to 110° C. for hours with stirring. After the completion of the reaction was confirmed on plates (ethyl acetate:n-hexane=1:5), ethyl acetate (30 mL) was added to dissolve the reaction mixture. After the ethyl acetate layer was washed with water (20 mL×2) and saturated saline solution (10 mL), the washed layer was then dried using magnesium sulfate. The solvent was distilled off under reduced pressure to yield crude crystal (185 mg). Flash column chromatography (ethyl acetate:n-hexane=1:6) yielded yellow plate-like crystal of Intermediate G (152 mg, 69%).

$^1$H NMR (500 MHz, CDCl$_3$) δ 8.95 (s, 2 H, Ar—H), 7.39 (br s, 1 H, NH), 7.34 (d, 1 H, J=2.0 Hz, Ar—H), 7.16 (d, 1 H, J=8.0 Hz, Ar—H), 6.99 (dd, 1 H, J=8.0 Hz and 2.0 Hz, Ar—H), 4.56 (sept, 1 H, J=6.0 Hz, OCH(CH$_3$)$_2$), 4.37 (q, 2 H, J=7.0 Hz, CO$_2$CH$_2$CH$_3$), 3.28 (sept, 1 H, J=7.0 Hz, CH(CH$_3$)$_2$), 1.39 (t, 3 H, J=7.0 Hz, CO$_2$CH$_2$CH$_3$), 1.37 (d, 6 H, J=6.0 Hz, OCH(CH$_3$)$_2$), 1.20 (d, 6 H, J=7.0 Hz, CH(CH$_3$)$_2$).

2) Synthesis of Intermediate H

After sodium hydride (60%, in oil) (40 mg, 1.0 mmol) was washed with n-hexane, anhydrous N,N-dimethylformamide (4 mL) was added for suspension, and then Intermediate G (137 mg, 0.4 mmol) was added, and the resultant solution was stirred for 10 minutes. Then, 1-iodoethane (32 μL, 0.4 mmol) was added, and further the resultant solution was stirred for an hour at room temperature. The reaction was followed up on TLC plates (ethyl acetate:n-hexane=1:5). The reaction solution was poured into water (50 mL), and the resultant solution was extracted with ethyl acetate (20 mL×3). The obtained organic layer was washed with water (30 mL×2) and saturated saline solution (30 mL) and was dried using magnesium sulfate. The solvent was distilled off under reduced pressure to yield colorless crystal of Intermediate H (78 mg, 86%).

$^1$H NMR (500 MHz, CDCl$_3$) δ 8.85 (s, 2 H, Ar—H), 7.23 (d, 1 H, J=8.0 Hz, Ar—H), 6.76 (dd, 1 H, J=8.0 Hz and 2.0 Hz, Ar—H), 6.68 (d, 1 H, J=2.0 Hz, Ar—H), 4.46 (sept, 1 H, J=6.0 Hz, OCH(CH$_3$)$_2$), 4.33 (q, 2 H, J=7.0 Hz, CO$_2$CH$_2$CH$_3$), 4.05 (q, 2 H, J=7.0 Hz, NCH$_2$CH$_3$), 3.30 (sept, 1 H, J=7.0 Hz, CH(CH$_3$)$_2$), 1.35 (t, 3 H, J=7.0 Hz, CO$_2$CH$_2$CH$_3$), 1.34 (d, 6 H, J=6.0 Hz, OCH(CH$_3$)$_2$), 1.25 (t, 3 H, J=7.0 Hz, NCH$_2$CH$_3$), 1.23 (d, 6 H, J=7.0 Hz, CH(CH$_3$)$_2$).

3) Synthesis of Target Compound 6a

Intermediate H (75 mg, 0.2 mmol) was dissolved in ethanol (2 mL), 2 N aqueous sodium hydroxide (2 mL) was added, and the resultant solution was stirred on water bath at 60° C. for 10 minutes. After the completion of the reaction was confirmed on TLC plates (ethyl acetate:n-hexane=1:5), the solution was poured into 2 N hydrochloric acid solution (20 mL), and the resultant solution was extracted with ethyl acetate (15 mL×2). After the obtained organic layer was washed with water (20 mL×2) and saturated saline solution (10 mL), the washed layer was dried using magnesium sulfate. The solvent was distilled off under reduced pressure to yield colorless residue of the target (67 mg, 97%).

$^1$H NMR (500 MHz, CDCl$_3$) δ 8.78 (s, 2 H, Ar—H), 7.17 (d, 1 H, J=8.0 Hz, Ar—H), 6.70 (dd, 1 H, J=8.0 Hz and 2.0 Hz, Ar—H), 6.51 (d, 1 H, J=2.0 Hz, Ar—H), 4.40 (sept, 1 H, J=6.0 Hz, OCH(CH$_3$)$_2$), 3.96 (q, 2 H, J=7.0 Hz, NCH$_2$CH$_3$), 3.26 (sept, 1 H, J=7.0 Hz, CH(CH$_3$)$_2$), 1.28 (d, 6 H, J=6.0 Hz, OCH(CH$_3$)$_2$), 1.19 (d, 6 H, J=7.0, CH(CH$_3$)$_2$), 1.11 (t, 3 H, J=7.0, NCH$_2$CH$_3$).

Mp 196.5-198.0° C.

FAB-MS m/e: 343 [M]$^+$, 344 [M+H]$^+$

Example 3

Synthesis of Target Compound 8

Figure 3:
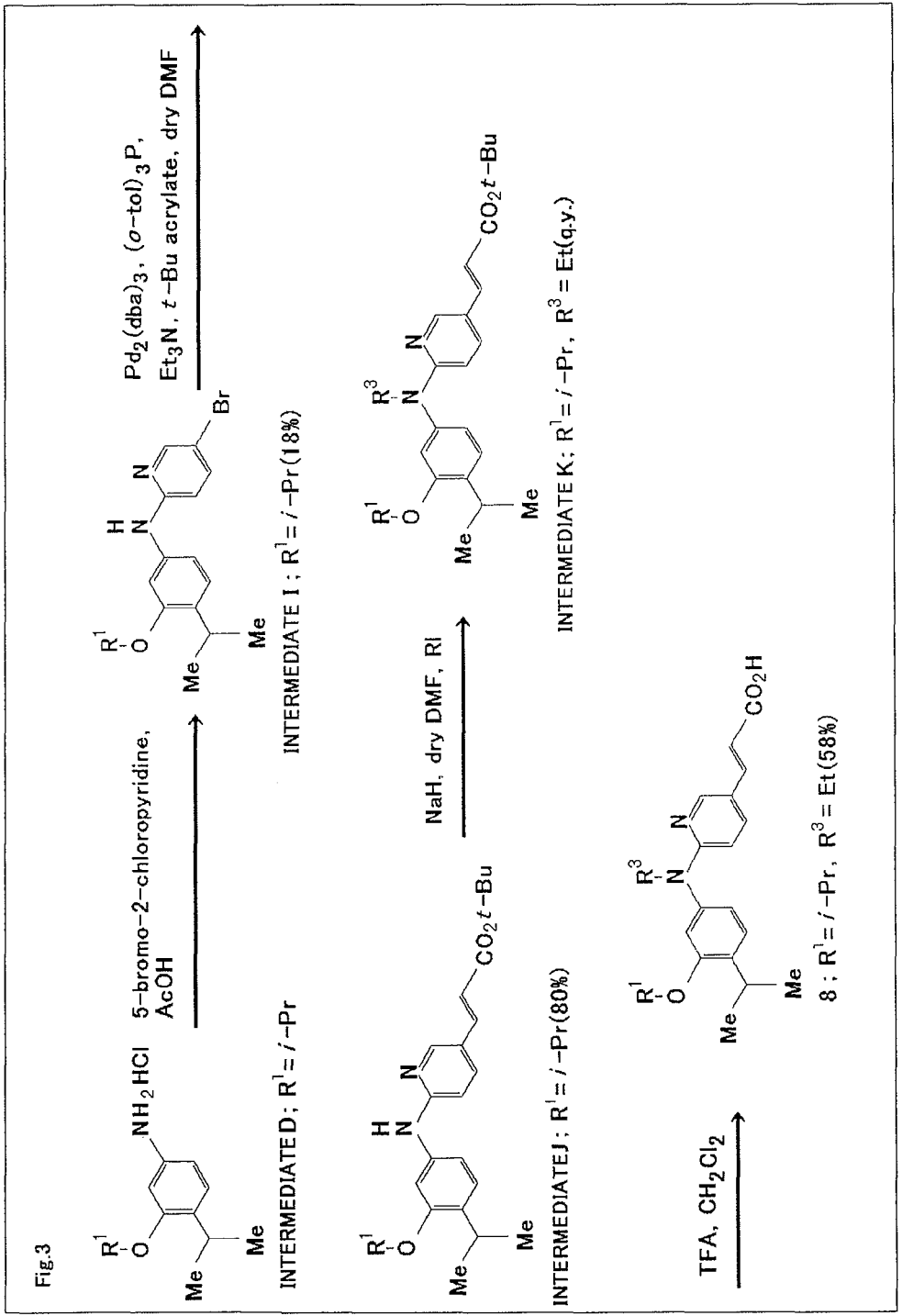
FIG. 3 shows the synthetic scheme of compound of Example 3.

The scheme of production method in this Example will be shown in FIG. 3.

1) Synthesis of Intermediate I

Intermediate D (181 mg, 0.7 mmol) and 5-bromo-2-chloropyridine (135 mg, 0.7 mmol) were dissolved in acetic acid (2.0 mL) and heated to 80° C. for 20 hours with stirring. After the completion of the reaction was confirmed on TLC plates (ethyl acetate:n-hexane=1:4), sodium bicarbonate aqueous solution was added to neutralize the solution, and the resultant solution was extracted with ethyl acetate (30 mL×3). The ethyl acetate layer was washed with water (50 mL×2) and saturated saline solution (50 mL) and was dried using magnesium sulfate. The solvent was distilled off under reduced pressure to yield crude crystal (244 mg). Flash column chromatography (ethyl acetate:n-hexane=1:6) yielded colorless crystal of Intermediate I (45 mg, 18%).

$^1$H NMR (300 MHz, CDCl$_3$) δ 8.20 (d, 1 H, J=2.5 Hz, Ar—H), 7.52 (dd, 1 H, J=9.0 Hz and 2.5 Hz, Ar—H), 7.14 (d, 1 H, J=8.0 Hz, Ar—H), 6.83 (d, 1 H, J=2.0 Hz, Ar—H), 6.77 (dd, 1 H, J=8.0 Hz and 2.0 Hz, Ar—H), 6.73 (d, 1 H, J=9.0 Hz, Ar—H), 6.43 (s, 1 H, NH), 4.49 (sept, 1 H, J=6.0 Hz, OCH(CH$_3$)$_2$), 3.27 (sept, 1 H, J=7.0 Hz, CH(CH$_3$)$_2$), 1.35 (d, 6 H, J=6.0 Hz, OCH(CH$_3$)$_2$), 1.20 (d, 6 H, J=7.0 Hz, CH(CH$_3$)$_2$).

2) Synthesis of Intermediate J

Intermediate I (106 mg, 0.30 mmol), Tris (dibenzylideneacetone) dipalladium (14 mg, 0.015 mmol), Tritolylphosphine (18 mg, 0.060 mmol) and triethylamine (0.205 mL, 1.5 mmol) were dissolved in anhydrous N,N-dimethylformamide (1.0 mL) under argon atmosphere, and then t-butyl acrylate (0.066 mL, 0.45 mmol) added thereto dropwise. This mixture was heated to 120° C. with stirring for 8 hours. After the completion of the reaction was confirmed on TLC plates (ethyl acetate:n-hexane=1:6), the reaction solution was filtered through celite, then the obtained filtrate was washed with water (30 mL×2) and saturated saline solution (30 mL) and was dried using magnesium sulfate. The solvent was distilled off under reduced pressure to yield crude crystal (190 mg). Flash column chromatography (ethyl acetate:n-hexane=1:4) yielded yellow crystal of Intermediate J (95 mg, 80%).

$^1$H NMR (300 MHz, CDCl$_3$) δ 8.28 (d, 1 H, J=2.5 Hz, Ar—H), 7.65 (dd, 1 H, J=9.0 Hz and 2.5 Hz, Ar—H), 7.50 (d, 1 H, J=16.0 Hz, Ar—H), 7.16 (d, 1 H, J=8.0 Hz, Ar—H), 6.87 (d, 1 H, J=2.0 Hz, Ar—H), 6.82 (dd, 1 H, J=8.0 Hz and 2.0 Hz, Ar—H), 6.83 (d, 1 H, J=9.0 Hz, Ar—H), 6.70 (s, 1 H, NH), 6.21 (d, 1 H, J=16.0 Hz, Ar—H), 4.53 (sept, 1 H, J=6.0 Hz, OCH(CH$_3$)$_2$), 3.28 (sept, 1 H, J=7.0 Hz, CH(CH$_3$)$_2$), 1.53 (s, 9 H, C(CH$_3$)$_3$), 1.35 (d, 6 H, J=6.0 Hz, OCH(CH$_3$)$_2$), 1.21 (d, 6 H, J=7.0 Hz, CH(CH$_3$)$_2$).

3) Synthesis of Intermediate K

After sodium hydride (60%, in oil) (8 mg, 0.20 mmol) was washed with n-hexane, anhydrous N,N-dimethylformamide (2 mL) was added for suspension, and then Intermediate J (55 mg, 0.13 mmol) was added, and the resultant solution was stirred for 5 minutes. Then, 1-iodoethane (20 μL, 0.25 mmol) was added, and further the resultant solution was stirred for 2.5 hours at room temperature. The reaction was followed up on TLC plates (ethyl acetate:n-hexane=1:6). The reaction solution was poured into water (50 mL), and the resultant solution was extracted with ethyl acetate (15 mL×3). After the obtained organic layer was washed with water (30 mL×2) and saturated saline solution (30 mL), the washed layer was then dried using magnesium sulfate. The solvent was distilled off under reduced pressure to yield residue (62 mg). Flash column chromatography (ethyl acetate:n-hexane=1:6) yielded yellow crystal of Intermediate K (59 mg, q.y.).

$^1$H NMR (300 MHz, CDCl$_3$) δ: 8.26 (d, 1 H, J=2.5 Hz, Ar—H), 7.49 (d, 1 H, J=16.0 Hz, Ar—H), 7.44 (dd, 1 H, J=9.0 Hz and 2.5 Hz, Ar—H), 7.24 (d, 1 H, J=8.0 Hz, Ar—H), 6.75 (dd, 1 H, J=8.0 Hz and 2.0 Hz, Ar—H), 6.66 (d, 1 H, J=2.0 Hz, Ar—H), 6.30 (d, 1 H, J=9.0 Hz, Ar—H), 6.11 (d, 1 H, J=16.0 Hz, Ar—H), 4.48 (sept, 1 H, J=6.0 Hz, OCH(CH$_3$)$_2$), 4.00 (q, 2 H, J=7.0 Hz, CO$_2$CH$_2$CH$_3$), 3.32 (sept, 1 H, J=7.0 Hz, CH(CH$_3$)$_2$), 1.52 (s, 9 H, C(CH$_3$)$_3$), 1.33 (d, 6 H, J=6.0 Hz, OCH(CH$_3$)$_2$), 1.24 (d, 6 H, J=7.0 Hz, CH(CH$_3$)$_2$), 1.23 (t, 3 H, J=7.0 Hz, CO$_2$CH$_2$CH$_3$).

4) Synthesis of Target Compound 8

Intermediate K (56 mg, 0.14 mmol) was dissolved in dichloromethane (1 mL), then trifluoroacetic acid (0.25 mL) was added, and the resultant solution was stirred for two hours at room temperature. After the completion of the reaction was confirmed on TLC plates (ethyl acetate:n-hexane=1:1), the solvent was distilled off from the reaction solution under reduced pressure. Recrystallization (dichloromethane/n-hexane) yielded white granular crystal of the target compound 8 (30 mg, 58%).

$^1$H NMR (500 MHz, CDCl$_3$) δ 8.54 (d, 1 H, J=2.5 Hz, Ar—H), 7.47 (d, 1 H, J=16.0 Hz, Ar—H), 7.76 (dd, 1 H, J=9.0 Hz and 2.5 Hz, Ar—H), 7.33 (d, 1 H, J=8.0 Hz, Ar—H), 6.74 (dd, 1 H, J=8.0 Hz and 2.0 Hz, Ar—H), 6.64 (d, 1 H, J=2.0 Hz, Ar—H), 6.57 (d, 1 H, J=9.0 Hz, Ar—H), 6.34 (d, 1 H, J=16.0 Hz, Ar—H), 4.51 (sept, 1 H, J=6.0 Hz, OCH(CH$_3$)$_2$), 4.07 (q, 2 H, J=7.0 Hz, CO$_2$CH$_2$CH$_3$), 3.34 (sept, 1 H, J=7.0 Hz, CH(CH$_3$)$_2$), 1.36 (d, 6 H, J=6.0 Hz, OCH(CH$_3$)$_2$), 1.34 (t, 3 H, J=7.0 Hz, CO$_2$CH$_2$CH$_3$), 1.24 (d, 6 H, J=7.0 Hz, CH(CH$_3$)$_2$).

Mp 137.5-139.2° C.

FAB-MS m/e: 369 [M+H]$^+$

Example 4

Synthesis of Target Compound 3a

The production scheme in this Example will be shown in FIG. 1.

1) Synthesis of Intermediate L

Intermediate B (906 mg, 5 mmol) was dissolved in anhydrous N,N-dimethylformamide (5.0 mL), and the resultant solution was mixed with potassium carbonate (1.4 g, 10 mmol), 1-bromo-2-methylpropane (863 μL, 8 mmol) and potassium iodide (166 mg) under stirring, which was then heated for 12 hours with stirring. After the completion of the reaction was confirmed on TLC plates (ethyl acetate:n-hexane=1:5), the solution was poured into water (70 mL), and extraction was carried out with ethyl acetate (40 mL×2). After organic layer was washed with water (50 mL×2) and saturated saline solution (40 mL) and was then dried using magnesium sulfate, the solvent was distilled off under reduced pressure to yield orange oil residue. Flash column chromatography (ethyl acetate:n-hexane=1:10) yielded yellow oil of Intermediate L (882 mg, 740).

$^1$H NMR (300 MHz, CDCl$_3$) δ 7.80 (dd, 1 H, J=8.5 and 2.5 Hz, Ar—H), 7.65 (d, 1 H, J=2.5 Hz, Ar—H), 7.32 (d, 1 H, J=8.5 Hz, Ar—H), 3.82 (d, 2 H, J=6.5 Hz, OCH$_2$CH(CH$_3$)$_2$), 3.40 (sep, 1 H, J=7.0 Hz, CH(CH$_3$)$_2$), 2.17 (m, 1 H, OCH$_2$CH(CH$_3$)$_2$), 1.25 (d, 6H, J=7.0 Hz, CH(CH$_3$)$_2$), 1.08 (d, 6 H, J=6.5 Hz, OCH$_2$CH$_2$(CH$_3$)$_2$).

2) Synthesis of Intermediate M

Intermediate L (880 mg, 3.7 mmol) was dissolved in methanol (10 mL), then an appropriate amount of palladium carbon was added, and the resultant solution was vigorously stirred for an hour at room temperature under hydrogen atmosphere. After the completion of the reaction was confirmed on TLC plates (ethyl acetate:n-hexane=1:5), filtration was carried out with celite and concentration was carried out under reduced pressure. Ethyl acetate (30 mL) was added thereto, and the deposited crystal was filtered to yield colorless needle crystal of Intermediate M (808 mg, 89%).

$^1$H NMR (300 MHz, CDCl$_3$) δ 6.98 (br s, 2H, NH$_2$), 7.23 (d, 1 H, J=8.0 Hz, Ar—H), 6.81 (s, 1 H, Ar—H), 6.80 (d, 1 H, J=8.0 Hz, Ar—H), 3.73 (d, 2 H, J=6.5 Hz, OCH$_2$CH(CH$_3$)$_2$), 3.22 (sep, 1 H, J=6.5 Hz, CH(CH$_3$)$_2$), 2.08 (m, 1 H, OCH$_2$CH(CH$_3$)$_2$), 1.16 (d, 6 H, J=6.5 Hz, CH(CH$_3$)$_2$), 1.02 (d, 6 H, J=6.5 Hz, OCH$_2$CH$_2$ (CH$_3$)$_2$).

3) Synthesis of Intermediate N

Intermediate M (390 mg, 1.6 mmol) and 6-chloronicotinic acid methyl ester (275 mg, 1.6 mmol) were dissolved in acetic acid (10 mL), and then the resultant solution was heated under reflux for 3 hours at 120° C. After the completion of the reaction was confirmed on TLC plates (ethyl acetate:n-hexane=1:5), the reaction solution was poured into saturated sodium bicarbonate aqueous solution (40 mL), and then the resultant solution was extracted with ethyl acetate (30 mL×2). After organic layer was washed with water (50 mL×2) and was dried using magnesium sulfate, the solvent was distilled off under reduced pressure to yield brown oil residue. Flash column chromatography (ethyl acetate:n-hexane=1:5) yielded colorless solid of Intermediate N (363 mg, 66%).

$^1$H NMR (300 MHz, CDCl$_3$) δ 8.81 (d, 1 H, J=2.0 Hz, Ar—H), 8.03 (dd, 1 H, J=9.0 and 2.0 Hz, Ar—H), 6.96 (d, 1 H, J=8.0 Hz, Ar—H), 6.78 (d, 1 H, J=9.0 Hz, Ar—H), 6.25 (dd, 1 H, J=8.0 and 2.0 Hz, Ar—H), 6.20 (d, 1 H, J=2.0 Hz, Ar—H), 3.89 (s, 3 H, CO$_2$CH$_3$), 3.67 (d, 2 H, J=6.5 Hz, OCH$_2$CH(CH$_3$)$_2$), 3.53 (br s, 1 H, NH), 3.22 (sep, 1 H, J=6.5 Hz, CH(CH$_3$)$_2$), 2.09 (m, 1 H, OCH$_2$CH(CH$_3$)$_2$), 1.18 (d, 6 H, J=6.5 Hz, CH(CH$_3$)$_2$), 1.04 (d, 6 H, J=6.5 Hz, OCH$_2$CH$_2$ (CH$_3$)$_2$).

4) Synthesis of Target Compound 3a

After sodium hydride (60%, in oil) (40 mg, 1.0 mmol) was washed with n-hexane and suspended in anhydrous N,N-dimethylformamide (5 mL), Intermediate (198 mg, 0.58 mmol) was added, and then the resultant solution was stirred for 10 minutes. Then, iodoethane (50 μL, 0.60 mmol) was added and stirred for an hour at room temperature. After the completion of the reaction was confirmed on TLC plates (ethyl acetate:n-hexane=1:5), the solution was poured into 2 N hydrochloric acid (30 mL), and then extraction was carried out with ethyl acetate (20 mL×2). After the obtained organic layer was washed with water (30 mL×2), the washed layer was dried using magnesium sulfate and the solvent was then distilled off under reduced pressure to yield yellow oil residue.

The obtained residue was dissolved in methanol (4 mL), 2 N aqueous sodium hydroxide (2 mL) was added, and the resultant solution was stirred for 5 minutes on water bath at 60° C. After the completion of the reaction was confirmed on TLC plates (ethyl acetate:n-hexane=1:5), the solution was poured into 2 N hydrochloric acid (30 mL), and then extraction was carried out with ethyl acetate (20 mL×2). The obtained organic layer was washed with water (20 mL×2) and saturated saline solution (20 mL), was dried using magnesium sulfate, and then the solvent was distilled off under reduced pressure to yield yellow residue. Flash column chromatography (ethyl acetate:n-hexane=1:3) yielded colorless solid of the target compound 3a (147 mg, 73%).

$^1$H NMR (300 MHz, CDCl$_3$) δ 8.91 (d, 1 H, J=2.0 Hz, Ar—H), 7.83 (dd, 1 H, J=9.0 and 2.0 Hz, Ar—H), 7.26 (d, 1 H, J=8.0 Hz, Ar—H), 6.77 (dd, 1 H, J=8.0 and 2.0 Hz, Ar—H), 6.64 (d, 1 H, J=2.0 Hz, Ar—H), 6.25 (d, 1 H, J=9.0 Hz, Ar—H), 4.04 (q, 2 H, J=7.0 Hz, NCH$_2$CH$_3$), 3.68 (d, 2 H, J=6.5 Hz, OCH$_2$CH(CH$_3$)$_2$), 3.36 (sep, 1 H, J=7.0 Hz, CH(CH$_3$)$_2$), 2.12 (m, 1 H, OCH$_2$CH(CH$_3$)$_2$), 1.26 (d, 6 H, J=7.0 Hz, CH(CH$_3$)$_2$), 1.25 (t, 3 H, J=7.0 Hz, NCH$_2$CH$_3$), 1.06 (d, 6 H, J=6.5 Hz, OCH$_2$CH(CH$_3$)$_2$).

Mp 191.5-193.0° C.

Anal. Calcd for C$_{21}$H$_{28}$N$_2$O$_3$·¼H$_2$O: C, 69.98; H, 8.33; N, 7.59.

Found: C, 70.01; H, 8.56; N, 7.46.

Example 5

Synthesis of Target Compound 7a

The production scheme in this Example will be shown in FIG. 2.

1) Synthesis of Intermediate P

To the mixture of 2-chloropyrimidine-5-carboxylic acid ethyl ester (200 mg, 1.1 mmol), Intermediate M (253 mg, 1.1 mmol) and potassium carbonate (912 mg, 6.6 mmol), N,N-dimethylformamide (5 drops) was added, and then the resultant solution was heated to 120° C. for 17 hours with stirring. After the completion of the reaction was confirmed on TLC plates (ethyl acetate:n-hexane=1:20), the solution was poured into 2 N hydrochloric acid (40 mL) and extraction was carried out with ethyl acetate (40 mL×3). After organic layer was washed with water (50 mL×2) and saturated saline solution (50 mL), the washed layer was dried using magnesium sulfate and the solvent was distilled off under reduced pressure. The obtained residue was applied to flash column chromatography (ethyl acetate:n-hexane=1:20) to yield colorless solid of Intermediate P (129 mg, 33%).

$^1$H NMR (300 MHz, CDCl$_3$) δ 8.95 (s, 2 H, Ar—H), 7.46 (s, 1 H, NH), 7.26 (d, 1 H, J=2.5 Hz, Ar—H), 7.17 (d, 1 H, J=8.5 Hz, Ar—H), 7.03 (dd, 1 H, J=8.5 and 2.5 Hz, Ar—H), 4.38 (q, 2 H, J=7.0 Hz, CO$_2$CH$_2$CH$_3$), 3.76 (d, 2 H, J=6.5 Hz, OCH$_2$CH(CH$_3$)$_2$), 3.31 (m, 1 H, OCH$_2$CH(CH$_3$)$_2$), 2.44 (sep, 1 H, CH(CH$_3$)$_2$), 1.39 (t, 3 H, J=7.0 Hz, CO$_2$CH$_2$CH$_3$), 1.22 (d, 6 H, J=7.0 Hz, OCH$_2$CH(CH$_3$)$_2$), 1.07 (d, 6 H, J=7.0 Hz, CH(CH$_3$)$_2$).

2) Synthesis of Target Compound 7a

After sodium hydride (60%, in oil) (28 mg, 0.7 mmol) was washed with n-hexane and suspended in anhydrous N,N-dimethylformamide (1 mL), a solution of Intermediate G (125 mg, 0.35 mmol) in anhydrous N,N-dimethylformamide (3 mL) was added, and then the resultant solution was stirred for 10 minutes at room temperature. Then, iodoethane (56 μL, 0.7 mmol) was added, and then the resultant solution was stirred for 10 minutes at room temperature. After the completion of the reaction was confirmed on TLC plates (ethyl acetate:n-hexane=1:10), the solution was poured into water (50 mL) and then the resultant solution was extracted with ethyl acetate (40 mL×3). After organic layer was washed with water (40 mL×2) and saturated saline solution (40 mL), the washed layer was dried using magnesium sulfate and then the solvent was distilled off under reduced pressure to yield colorless solid of Intermediate Q (114 mg, 76%).

The obtained Intermediate Q (110 mg, 0.29 mmol) was dissolved in ethanol (6 mL), then 2 N aqueous sodium hydroxide (6 mL) was added, and the resultant solution was stirred for an hour on water bath at 60° C. After the completion of the reaction was confirmed on TLC plates (ethyl acetate:n-hexane=1:3), neutralization was performed with 2 N hydrochloric acid, and then the resultant solution was extracted with ethyl acetate (40 mL×3). After organic layer was washed with water (40 mL×2) and saturated saline solution (40 mL) and was then dried using magnesium sulfate, the solvent was distilled off under reduced pressure. The obtained residue was applied on flash column chromatography (ethyl acetate:n-hexane=1:1) to yield colorless solid target compound 7a (86 mg, 69%).

$^1$H NMR (300 MHz, CDCl$_3$) δ 8.89 (s, 2 H, Ar—H), 7.26 (d, 1 H, J=8.0 Hz, Ar—H), 6.79 (dd, 1 H, J=8.0 and 2.0 Hz, Ar—H), 6.66 (d, 1 H, J=2.0 Hz, Ar—H), 4.06 (q, 2 H, J=7.0 Hz, NCH$_2$CH$_3$), 3.69 (d, 2 H, J=6.5 Hz, OCH$_2$CH(CH$_3$)$_2$), 3.34 (m, 1 H, OCH$_2$CH(CH$_3$)$_2$), 2.11 (sep, 1 H, CH(CH$_3$)$_2$), 1.28 (t, 3 H, J=7.0 Hz, NCH$_2$CH$_3$), 1.25 (d, 6 H, J=7.0 Hz, OCH$_2$CH(CH$_3$)$_2$), 1.05 (d, 6 H, J=6.5 Hz, CH(CH$_3$)$_2$).

Mp 180.5-182.0° C.

Anal. Calcd for C$_{20}$H$_{27}$N$_3$O$_3$: C, 67.20; H, 7.61; N, 11.76.

Found: C, 67.01; H, 7.25; N, 11.60.

General formula XII:
[Compound 12]

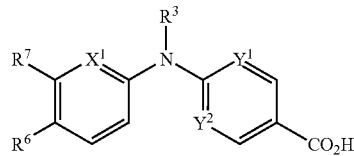

Formula (XII)

TABLE 2

| Compound | R$^7$ | R$^6$ | R$^3$ | X$^1$ | Y$^1$ | Y$^2$ | ClogP |
|---|---|---|---|---|---|---|---|
| 1a (NEt-3IP) | O-i-Pr | i-Pr | Et | CH | N | CH | 5.61 |
| 1b | O-i-Pr | i-Pr | Ms | CH | N | CH | 4.28 |
| 1c | O-i-Pr | i-Pr | H | CH | N | CH | 5.11 |
| 2a | O-n-Pr | i-Pr | Et | CH | N | CH | 5.83 |
| 2b | O-n-Pr | i-Pr | Ms | CH | N | CH | 4.50 |
| 2c | O-n-Pr | i-Pr | H | CH | N | CH | 5.33 |
| 3a (NEt-3IB) | O-i-Bu | i-Pr | Et | CH | N | CH | 6.23 |
| 4a (NEt-4IP) | i-Pr | O-i-Pr | Et | CH | N | CH | 5.61 |
| 4c | i-Pr | O-i-Pr | H | CH | N | CH | 5.11 |
| 5c | i-Pr | O-n-Pr | H | CH | N | CH | 5.33 |
| 6a (PEt-3IP) | O-i-Pr | i-Pr | Et | CH | N | N | 4.89 |
| 7a (PEt-3IB) | O-i-Bu | i-Pr | Et | CH | N | N | 5.50 |

Example 6

Synthesis of Target Compound 9 (BEt-3IP)

Figure 4:
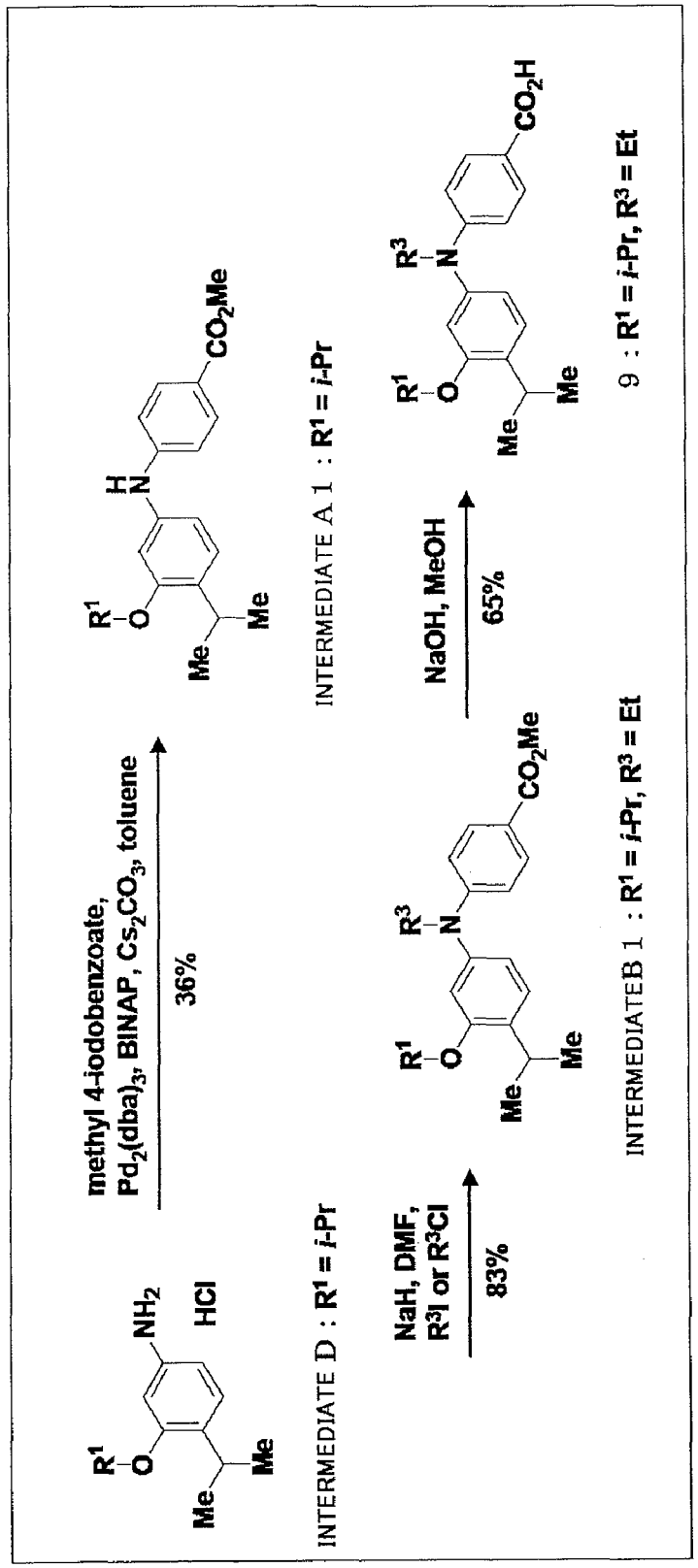
FIG. 4 shows the synthetic scheme of compound of Example 6.

The scheme of production method in this Example will be shown in FIG. 4.

1) Synthesis of Intermediate A1

After 4-iodobenzoic acid methyl ester (524 mg, 2.0 mmol) and Intermediate D (460 mg, 2.0 mmol) were dissolved in anhydrous toluene (20 mL), and Tris (dibenzylideneacetone) dipalladium (92 mg, 5.0 mol %), (±)-BINAP (93 mg, 7.5 mol %) and cesium carbonate (1.56 g, 4.8 mmol) were added thereto, the mixture was heated over night under reflux at 110° C. under Ar atmosphere. After the completion of the reaction was confirmed on TLC plates (ethyl acetate:n-hexane=1:3), precipitate was filtered through celite. The filtrate was distilled off under reduced pressure and was applied to flash column chromatography (ethyl acetate:n-hexane=1:5) to yield brown oil of Intermediate A1 (234 mg, 36%).

$^1$H NMR (500 MHz, CDCl$_3$) δ 7.89 (dd, 2 H, J=7.0 and 2.0 Hz, Ar—H), 7.14 (d, 1 H, J=8.0 Hz, Ar—H), 6.94 (dd, 2 H, J=7.0 and 2.0 Hz, Ar—H), 6.70 (dd, 1 H, J=8.0 and 2.0 Hz, Ar—H), 6.68 (d, 1 H, J=2.0 Hz, Ar—H), 5.92 (s, 1 H, NH), 4.47 (sept, 1 H, J=6.0 Hz, OCH(CH$_3$)$_2$), 3.87 (s, 3 H, CO$_2$CH$_3$), 3.27 (sept, 1 H, J=7.0 Hz, CH(CH$_3$)$_2$), 1.34 (d, 6 H, J=6.0 Hz, OCH(CH$_3$)$_2$), 1.21 (d, 6 H, J=7.0 Hz, CH(CHH$_3$)$_2$).

2) Intermediate B1

After sodium hydride (40 mg, 1.0 mmol) was suspended in anhydrous N,N-dimethylformamide (5 mL), Intermediate A1 (234 mg, 0.7 mmol) was added thereto and the resultant solution was stirred for 5 minutes at room temperature under Ar atmosphere. Then, iodoethane (80 µL, 1.0 mmol) was added to the reaction solution and was stirred for another 5 minutes at room temperature under Ar atmosphere. After the completion of the reaction was confirmed on TLC plates (ethyl acetate:n-hexane=1:5), the reaction solution was poured into 2 N hydrochloric acid (30 mL), and then extraction was carried out with ethyl acetate (25 mL×2). After the obtained organic layer was washed with water (30 mL) and saturated saline solution (20 mL), the washed layer was then dried using magnesium sulfate. The solvent was distilled off under reduced pressure to yield yellow residue (246 mg). The obtained residue was applied to flash column chromatography (ethyl acetate:n-hexane=1:5) yielded colorless oil of Intermediate B1 (212 mg, 83%).

$^1$H NMR (300 MHz, CDCl$_3$) δ 7.82 (dd, 2 H, J=7.0 and 2.0 Hz, Ar—H), 7.21 (d, 1 H, J=8.0 Hz, Ar—H), 6.72 (dd, 1 H, J=8.0 and 2.0 Hz, Ar—H), 6.66 (dd, 2 H, J=7.0 and 2.0 Hz, Ar—H), 6.64 (d, 1 H, J=2.0 Hz, Ar—H), 4.45 (sept, 1 H, J=6.0 Hz, OCH(CH$_3$)$_2$), 3.85 (s, 3 H, CO$_2$CH$_3$), 3.77 (q, 2 H, J=7.0 Hz, NCH$_2$CH$_3$), 3.31 (sept, 1 H, J=7.0 Hz, CH(CH$_3$)$_2$), 1.31 (d, 6 H, J=6.0 Hz, OCH(CH$_3$)$_2$), 1.24 (t, 3 H, J=7.0 Hz, NCH$_2$CH$_3$), 1.23 (d, 6 H, J=7.0 Hz, CH(CH$_3$)$_2$).

7) Synthesis of Target Compound 9 (BEt-3IP)

Intermediate B1 (212 mg, 0.6 mmol.) was dissolved in methanol (15 mL), then 2 N aqueous sodium hydroxide (10 mL) was added, and the resultant solution was stirred for an hour on water bath at 60° C. After the completion of the reaction was confirmed on TLC plates (ethyl acetate:n-hexane=1:2), neutralization was performed with 2 N hydrochloric acid (10 mL). The neutralized reaction solution was poured into water (40 mL), and then the resultant solution was extracted with ethyl acetate (30 mL×2). After the obtained organic layer was washed with water (50 mL) and saturated saline solution (30 mL), the washed layer was then dried using magnesium sulfate. The solvent was distilled off under reduced pressure to yield colorless residue (229 mg) of the target. Recrystallization (dichloromethane/n-hexane) yielded colorless needle crystal of the target compound 9 (133 mg, 65%).

$^1$H NMR (300 MHz, DMSO-d6) δ 7.70 (d, 2 H, J=9.0 Hz, Ar—H), 7.24 (d, 1 H, J=8.5 Hz, Ar—H), 6.75 (d, 1 H, J=2.0 Hz, Ar—H), 6.72 (dd, 1 H, J=8.5 and 2.0 Hz, Ar—H), 6.67 (d, 2 H, J=9.0 Hz, Ar—H), 4.55 (sept, 1 H, J=6.0 Hz, OCH(CH$_3$)$_2$), 3.75 (q, 2 H, J=7.0 Hz, NCH$_2$CH$_3$), 3.22 (sept, 1 H, J=7.0 Hz, CH(CH$_3$)$_2$), 1.25 (d, 6 H, J=6.0 Hz, OCH(CH$_3$)$_2$), 1.18 (d, 6 H, J=7.0 Hz, CH(CH$_3$)$_2$), 1.15 (t, 3 H, J=7.0 Hz, NCH$_2$CH$_3$).

Example 7

Synthesis of Target Compound 10

Figure 5:
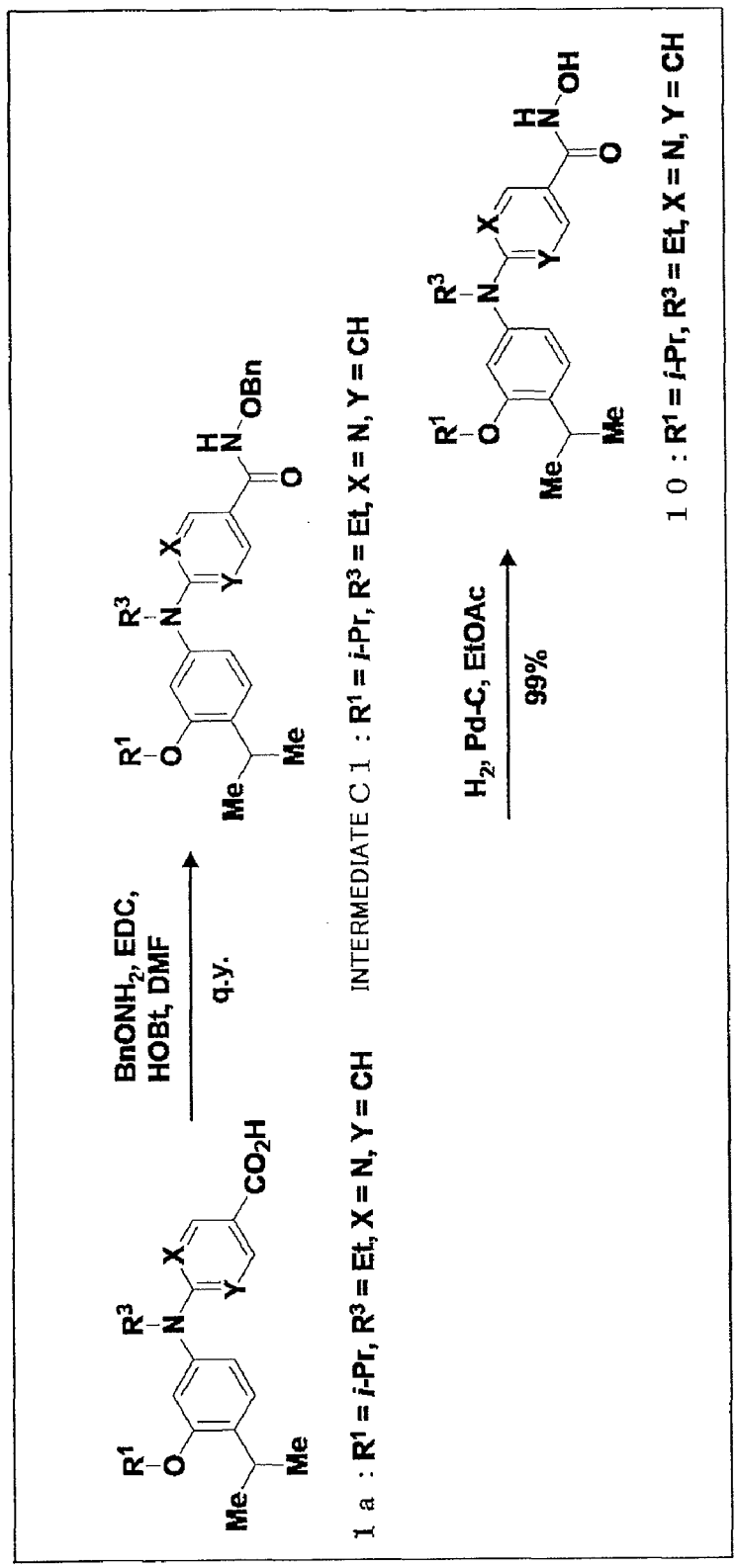
FIG. 5 shows the synthetic scheme of compound of Example 7.

The scheme of production method in this Example will be shown in FIG. 5.

1) Synthesis of Intermediate C1

After compound 1a (182 mg, 0.5 mmol) was dissolved in anhydrous N,N-dimethylformamide (2.0 mL), then O-benzylhydroxylamine (65 mg, 0.5 mmol), 1-hydroxybenzotriazole monohydrate (90 mg, 0.6 mmol), 1-ethyl-3-(3-dimethylaminopropyl)carbodiimide hydrochloride (123 mg, 0.6 mmol) and anhydrous triethylamine (74 µL, 0.5 mmol) were added, and then the resultant solution was stirred for 5 hours at room temperature. After the completion of the reaction was confirmed on TLC plates (ethyl acetate:n-hexane=1:2), the solution was poured into water (20 mL), and then the resultant solution was extracted with ethyl acetate (20 mL×2). Organic layer was washed with water (20 mL) and saturated saline solution (20 mL). After the obtained organic layer was dried using magnesium sulfate, the solvent was distilled off under reduced pressure to yield crude product (366 mg). Flash column chromatography (ethyl acetate:n-hexane=1:2→1:1) yielded colorless needle crystal of Intermediate C1 (277 mg, q.y.).

$^1$H NMR (500 MHz, CDCl$_3$) δ 8.46 (d, 1 H, J=2.0 Hz, Ar—H), 8.22 (s, 1 H, NH), 7.60 (dd, 1 H, J=9.0 and 2.0 Hz, Ar—H), 7.44 (dd, 2 H, J=7.5 and 2.0 Hz, Ar—H), 7.41-7.36 (m, 3 H, Ar—H), 7.24 (d, 1 H, J=8.0 Hz, Ar—H), 6.72 (dd, 1 H, J=8.0 and 2.0 Hz, Ar—H), 6.63 (d, 1 H, J=2.0 Hz, Ar—H) 6.27 (d, 1 H, J=9.0 Hz, Ar—H), 5.00 (s, 2 H, CH$_2$Ph), 4.46 (sept, 1 H, J=6.0 Hz, OCH(CH$_3$)$_2$), 3.98 (q, 2 H, J=7.0 Hz, NCH$_2$CH$_3$), 3.31 (sept, 1 H, J=7.0 Hz, CH(CH$_3$)$_2$), 1.33 (d, 6 H, J=6.0 Hz, OCH(CH$_3$)$_2$), 1.23 (d, 6 H, J=7.0 Hz, CH(CH$_3$)$_2$), 1.22 (t, 3 H, J=7.0 Hz, NCH$_2$CH$_3$).

2) Synthesis of Target Compound 10

Intermediate C1 (185 mg, 0.4 mmol) was dissolved in ethyl acetate (5.0 mL), then an appropriate amount of palladium carbon was added, and the resultant solution was stirred for an hour at room temperature under hydrogen atmosphere. After the completion of the reaction was confirmed on TLC plates (ethyl acetate:n-hexane=1:2), filtration was carried out with celite and the solvent was distilled off under reduced pressure to yield residue (212 mg). Recrystallization (ethyl acetate/n-hexane) yielded white spherical crystal of the target compound 10 (146 mg, 99%).

$^1$H NMR (300 MHz, DMSO-d6) δ 10.95 (br s, 1 H, OH), 8.85 (br s, 1 H, NH), 8.51 (d, 1 H, J=2.5 Hz, Ar—H), 7.69 (dd, 1 H, J=9.0 and 2.5 Hz, Ar—H), 7.27 (d, 1 H, J=8.0 Hz, Ar—H), 6.80 (s, 1 H, Ar—H), 6.78 (d, 1 H, J=8.0 Hz, Ar—H), 6.23 (d, 1 H, J=9.0 Hz, Ar—H), 4.60 (1 H, sept, J=6.0 Hz, OCH(CH$_3$)$_2$), 3.97 (sept, 1 H, J=7.0 Hz, CH(CH$_3$)$_2$), 3.32 (q, 2 H, J=7.0 Hz, NCH$_2$CH$_3$), 1.27 (d, 6 H, J=6.0 Hz, OCH(CH$_3$)$_2$), 1.20 (d, 6 H, J=7.0 Hz, CH(CH$_3$)$_2$), 1.16 (t, 3 H, J=7.0 Hz, NCH$_2$CH$_3$).

Mp 153.0-155.5° C.

FAB-MS m/e: 358 [M+H]$^+$

Example 8

Synthesis of Target Compound 11

Figure 6:
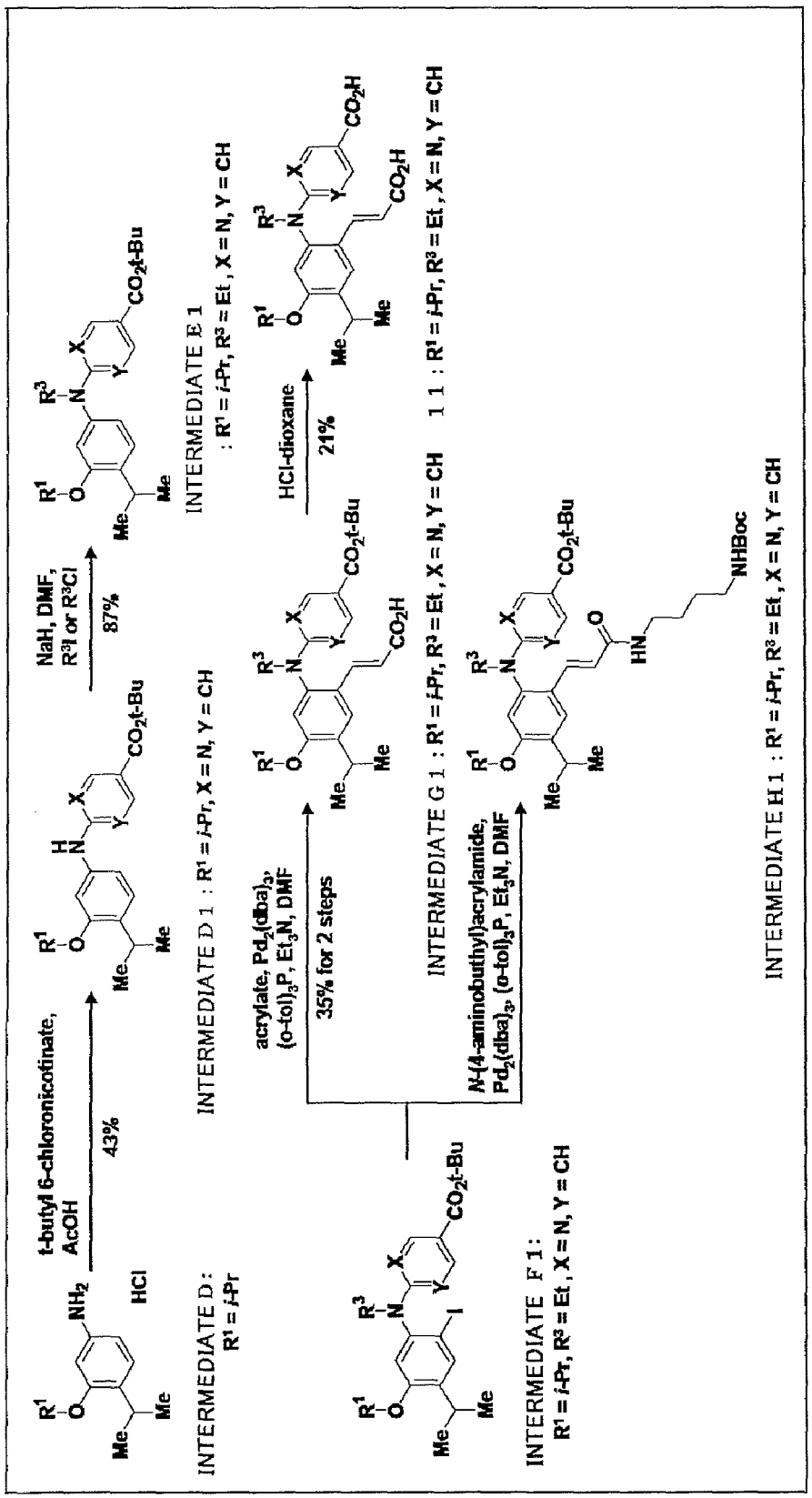
FIG. 6 shows the synthetic scheme of compound of Example 8.

The scheme of production method in this Example will be shown in FIG. 6.

1) Synthesis of Intermediate D1

Intermediate D (230 mg, 1.0 mmol) and 6-chloronicotinic acid t-butyl ester (214 mg, 1.0 mmol) were dissolved in anhydrous dioxane (5 mL), then p-toluenesulfonic acid monohydrate (19 mg, 0.1 mmol) was added, and the resultant solution was heated under reflux at 100° C. for 22 hours. After the completion of the reaction was confirmed on TLC plates (ethyl acetate:n-hexane=1:5), the solution was poured into saturated sodium bicarbonate solution (40 mL), and then the resultant solution was extracted with ethyl acetate (30 mL×3). After organic layer was washed with water (70 mL) and saturated saline solution (30 mL), the washed layer was then dried using magnesium sulfate, and the solvent was then distilled off under reduced pressure. Flash column chromatography (ethyl acetate:n-hexane=1:6→1:5) yielded white solid of Intermediate D1 (158 mg, 43%).

$^1$H NMR (500 MHz, CDCl$_3$) δ: 8.76 (d, 1 H, J=2.0 Hz), 7.98 (dd, 1 H, J=9.0 and 2.0 Hz), 7.16 (d, 1 H, J=8.0 Hz), 6.87 (d, 1 H, J=2.0 Hz), 6.81 (dd, 1 H, J=8.0 and 2.0 Hz), 6.80 (br s, 1 H), 6.76 (d, 1 H, J=9.0 Hz), 4.51 (sept, 1 H, J=6.0 Hz), 3.28 (sept, 1 H, J=7.0 Hz), 1.58 (s, 9 H), 1.35 (d, 6 H, J=6.0 Hz), 1.21 (d, 6 H, J=7.0 Hz).

2) Synthesis of Intermediate E1

After sodium hydride (60%, in oil) (28 mg, 0.7 mmol) was washed with n-hexane, the solution of Intermediate D1 (125 mg, 0.35 mmol) in anhydrous N,N-dimethylformamide (5 mL) was added, and then the resultant solution was stirred for 10 minutes at room temperature under Ar atmosphere. Then, iodoethane (45 µL, 0.56 mmol) was added, and then the resultant solution was stirred for 10 minutes at room temperature. After the completion of the reaction was confirmed on TLC plates (ethyl acetate:n-hexane=1:5), the solution was poured into water (90 mL), and then the resultant solution was extracted with ethyl acetate (40 mL×3). After organic layer was washed with water (40 mL×2) and saturated saline solution (30 mL), the washed layer was then dried using magnesium sulfate, and the solvent was then distilled off under reduced pressure. Flash column chromatography (ethyl acetate:n-hexane=1:8) yielded colorless oil of Intermediate E1 (121 mg, 87%).

$^1$H NMR (500 MHz, CDCl$_3$) δ 8.80 (d, 1 H, J=2.0 Hz), 7.76 (dd, 1 H, J=9.0 and 2.0 Hz), 7.24 (d, 1 H, J=8.0 Hz), 6.74 (dd, 1 H, J=8.0 and 2.0 Hz), 6.65 (d, 1 H, J=2.0 Hz), 6.24 (d, 1 H, J=9.0 Hz), 4.47 (sept, 1 H, J=6.0 Hz), 4.02 (q, 2 H, J=7.0 Hz), 3.31 (sept, 1 H, J=7.0 Hz), 1.55 (s, 9 H), 1.33 (d, 6 H, J=6.0 Hz), 1.23 (d, 6 H, J=7.0 Hz), 1.23 (t, 3 H, J=7.0 Hz).

3) Synthesis of Intermediate F1

Intermediate E1 (744 mg, 1.9 mmol) was dissolved in methanol (50 mL), and calcium carbonate (281 mg, 2.8 mmol) was added and suspended in H$_2$O (20 mL). The solution of ICl (103 µL, 2.1 mmol) in methanol (50 mL) was added dropwise and stirred for 16 hours at room temperature. After the completion of the reaction was confirmed on TLC plates (ethyl acetate:n-hexane=1:10), the reaction solution was poured into water (80 mL), and then the resultant solution was extracted with ethyl acetate (50 mL×3). Organic layer was washed with water (100 mL) and saturated saline solution (30 mL). After the obtained organic layer was dried using magnesium sulfate, the solvent was distilled off under reduced pressure. Flash column chromatography (ethyl acetate:n-hexane=1:10) yielded brown oil of Intermediate F1 (818 mg).

$^1$H NMR (300 MHz, CDCl$_3$) δ 8.85 (d, 1 H, J=2.5 Hz), 7.81 (dd, 1 H, J=9.0 and 2.5 Hz), 7.68 (s, 1 H), 6.66 (s, 1 H), 5.96 (d, 1 H, J=9.0 Hz), 4.49-4.43 (m, 1 H), 4.36-4.32 (m, 1 H), 3.60-3.56 (m, 1 H), 3.26 (sept, 1 H, J=7.0 Hz), 1.55 (s, 9 H), 1.33-1.30 (m, 6 H), 1.28-1.21 (m, 9 H).

4) Synthesis of Intermediate G1

Acrylic acid (220 µL, 3.2 mmol) and triethylamine (446 µL, 3.2 mmol) were dissolved in anhydrous N,N-dimethylformamide (5.0 mL), and then Intermediate F1 (337 mg, 0.64 mmol), Tritolylphosphine (40 mg, 20 mol %) and Tris(dibenzylideneacetone)dipalladium (27 mg, 5 mol %) were added and heated to 120° C. for 10 hours with stirring under Ar atmosphere. After the completion of the reaction was confirmed on TLC plates (ethyl acetate:n-hexane=1:1), filtration was carried out with celite, and the solution was poured into water (80 mL), and then the resultant solution was extracted with ethyl acetate (50 mL×3). Organic layer was washed with water (50 mL) and saturated saline solution (30 mL). After the obtained organic layer was dried using magnesium sulfate, the solvent was distilled off under reduced pressure. Flash column chromatography (ethyl acetate:n-hexane=1:2) yielded colorless oil of Intermediate G1 (125 mg, 35% for 2 steps).

$^1$H NMR (500 MHz, CDCl$_3$) δ 8.83 (d, 1 H, J=2.4 Hz), 7.79 (dd, 1 H, J=8.9 and 2.4 Hz), 7.64 (d, 1 H, J=16.0 Hz), 7.59 (s, 1 H), 6.57 (s, 1 H), 6.31 (d, 1 H, J=16.0 Hz), 6.01 (d, 1 H, J=9.0 Hz), 4.52 (sept, 1 H, J=6.0 Hz), 4.22 (br s, 1 H), 3.71 (br s, 1 H), 3.30 (sept, 1 H J=7.0 Hz), 1.55 (s, 9 H), 1.33 (br s, 6 H), 1.27 (d, 6 H, J=7.0 Hz), 1.22 (t, 3 H, J=7.0 Hz).

5) Synthesis of Target Compound 11

Intermediate G1 was dissolved in 4 N hydrochloric acid-1,4-dioxane (3 mL), and then the resultant solution was heated to 40° C. for 15 hours with stirring. After the completion of the reaction was confirmed on TLC plates (ethyl acetate:n-hexane=2:1), the solution was poured into water (40 mL), and then the resultant solution was extracted with ethyl acetate (25 mL×3). Organic layer was washed with water (40 mL) and saturated saline solution (20 mL). After the obtained organic layer was dried using magnesium sulfate, the solvent was distilled off under reduced pressure. Flash column chromatography (ethyl acetate:n-hexane=2:1) yielded white solid target compound 11 (23 mg, 21%).

$^1$H NMR (500 MHz, CDCl$_3$) δ 12.37 (br s, 1 H), 8.70 (d, 1 H, J=2.0 Hz), 7.82 (dd, 1 H, J=9.0, 2.0 Hz), 7.77 (s, 1 H), 7.33 (d, 1 H, J=16.0 Hz), 6.87 (s, 1 H), 6.45 (d, 1 H, J=16.0 Hz), 6.02 (d, 1 H, J=9.0 Hz), 4.69 (sept, 1 H, J=6.0 Hz), 4.09 (br s, 1 H), 3.78 (br s, 1 H), 1.27-1.23 (m, 12 H), 1.14 (t, 3 H, J=7.0 Hz).

6) Synthesis of Intermediate H1

N-(4-aminobutyl)acrylamide (53 mg, 0.84 mmol) and triethylamine (58 µL, 0.42 mmol) were dissolved in anhydrous N,N-dimethylformamide (2.0 mL), then Intermediate F1 (102 mg, 0.42 mmol), Tritolylphosphine (5 mg, 20 mol %) and Tris(dibenzylideneacetone)dipalladium (4 mg, 5 mol %) were added, and then the resultant solution was heated to 120° C. for 19 hours with stirring under Ar atmosphere. After the completion of the reaction was confirmed on TLC plates (ethyl acetate:n-hexane=1:1), filtration was carried out with celite, then the solution was poured into water (60 mL), and then the resultant solution was extracted with ethyl acetate (30 mL×2). Organic layer was washed with water (30 mL×2) and saturated saline solution (20 mL). After the obtained organic layer was dried using magnesium sulfate, the solvent was distilled off under reduced pressure. Flash column chromatography (ethyl acetate:n-hexane=1:1→2:1→4:1) yielded white solid of Intermediate H1 (44 mg, 57% for 2 steps).

$^1$H NMR (500 MHz, CDCl$_3$) δ 8.82 (d, 1 H, J=1.5 Hz), 7.76 (dd, 1 H, J=9.0 and 1.5 Hz), 7.52 (s, 1H), 7.46 (d, 1 H, J=16.0 Hz), 6.55 (s, 1 H), 6.27 (d, 1 H, J=16.0 Hz), 6.02 (d, 1 H, J=9.0 Hz), 5.80 (br s, 1H), 4.60 (br s, 1H), 4.48 (m, 1 H), 4.30 (m, 1 H), 3.64 (m, 1H), 3.34-3.33 (m, 2H), 3.33 (sept, 1 H J=7.0 Hz), 3.13 (m, 2H), 1.54 (s, 9 H), 1.44 (s, 9H), 1.32 (m, 6H), 1.27-1.24 (m, 6H), 1.23 (t, 3H, J=7.0 Hz).

Example 9

Synthesis of Target Compound 12

Figure 7:
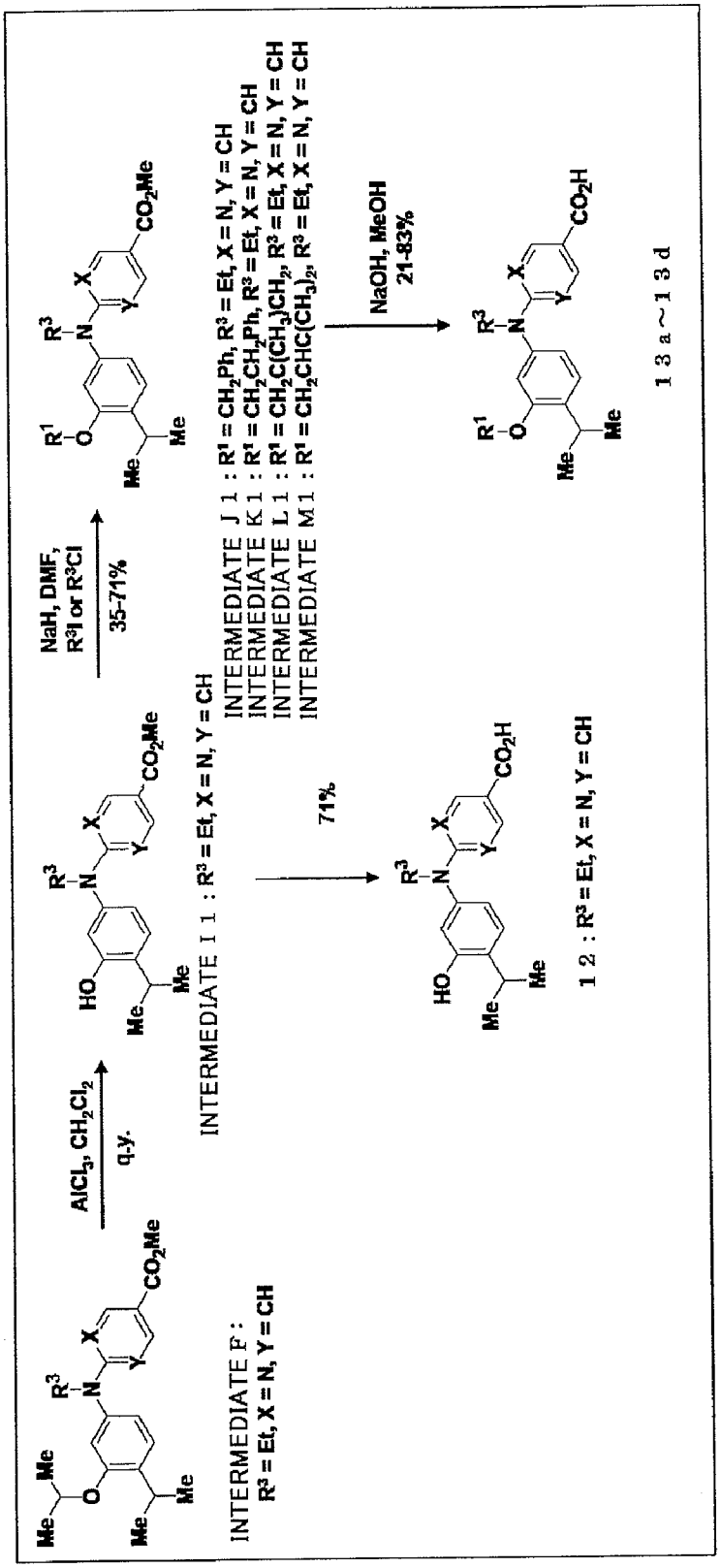
FIG. 7 shows the synthetic scheme of compounds of Examples 9 to 13.

The scheme of production method in this Example will be shown in FIG. 7.

1) Synthesis of Intermediate I1

Intermediate F (350 mg, 1.0 mmol) was dissolved in anhydrous dichloromethane (5.0 mL), then aluminum trichloride (400 mg, 3.0 mmol) was added, and the resultant solution was stirred for 7 hours at room temperature under argon atmosphere. After the completion of the reaction was confirmed on TLC plates (ethyl acetate:n-hexane=1:5), the solution was poured into 1 N hydrochloric acid (40 mL), and then the resultant solution was extracted with ethyl acetate (30 mL×2). Organic layer was washed with water (40 mL) and saturated saline solution (30 mL). After the obtained organic layer was dried using magnesium sulfate, the solvent was distilled off under reduced pressure to yield brown oil residue. Flash column chromatography (ethyl acetate:n-hexane=1:3) yielded colorless oil of Intermediate I1 (314 mg, q.y.).

$^1$H NMR (300 MHz, CDCl$_3$) δ 8.81 (d, 1 H, J=2.5 Hz, Ar—H), 7.79 (dd, 1 H, J=9.0 and 2.5 Hz, Ar—H), 7.24 (d, 1 H, J=8.0 Hz, Ar—H), 6.76 (dd, 1 H, J=8.0 and 2.0 Hz, Ar—H), 6.61 (d, 1 H, J=2.0 Hz, Ar—H), 6.27 (d, 1 H, J=9.0 Hz, Ar—H), 5.31 (s, 1 H, OH), 4.00 (q, 2 H, J=7.0 Hz, NCH$_2$CH$_3$), 3.86 (s, 3 H, CO$_2$CH$_3$), 3.23 (sept, 1 H, J=7.0 Hz, CH(CH$_3$)$_2$), 1.29 (d, 6 H, J=7.0 Hz, CH(CH$_3$)$_2$), 1.22 (t, 3 H, J=7.0 Hz, NCH$_2$CH$_3$).

2) Synthesis of Target Compound 12

Intermediate I1 (315 mg, 1.0 mmol) was dissolved in methanol (15 mL), then 2 N aqueous sodium hydroxide (10 mL) was added, and the resultant solution was stirred for 5 minutes on water bath at 60° C. After the completion of the reaction was confirmed on TLC plates (ethyl acetate:n-hexane=1:2), neutralization was performed with 2 N hydrochloric acid (10 mL). The neutralized reaction solution was poured into water (40 mL), and then the resultant solution was extracted with ethyl acetate (30 mL×2). The obtained organic layer was washed with water (50 mL) and saturated saline solution (30 mL), and was then dried using magnesium sulfate. The solvent was distilled off under reduced pressure to yield colorless residue (322 mg) of the target. Recrystallization (ethanol/n-hexane) yielded colorless needle crystal of the target compound 12 (214 mg, 71%).

$^1$H NMR (300 MHz, DMSO-d6) δ 12.46 (br s, 1 H, CO$_2$H), 9.57 (br s, 1 H, OH), 8.66 (d, 1 H, J=2.0 Hz, Ar—H), 7.79 (dd, 1 H, J=9.0 and 2.0 Hz, Ar—H), 7.22 (d, 1 H, J=7.5 Hz, Ar—H), 6.68 (dd, 1 H, J=7.5 and 2.0 Hz, Ar—H), 6.66 (d, 1 H, J=2.0 Hz, Ar—H), 6.25 (d, 1 H, J=9.0 Hz, Ar—H), 3.93 (q, 2 H, J=7.0 Hz, NCH$_2$CH$_3$), 3.21 (sept, 1 H, J=7.0 Hz, CH(CH$_3$)$_2$), 1.19 (d, 6 H, J=7.0 Hz, CH(CH$_3$)$_2$), 1.13 (t, 3 H, J=7.0 Hz, NCH$_2$CH$_3$).

Example 10

Synthesis of Target Compound 13a

The scheme of production method in this Example will be shown in FIG. 7.

1) Synthesis of Intermediate J1

After intermediate I1 (75 mg, 0.2 mmol) was dissolved in anhydrous N,N-dimethylformamide (3.0 mL), then potassium carbonate (69 mg, 0.5 mmol), an appropriate amount of potassium iodide and benzylbromide (59 μL, 0.5 mmol) were added, and then the resultant solution was heated to 60° C. for 2 hours with stirring under argon atmosphere. After the completion of the reaction was confirmed on TLC plates (ethyl acetate:n-hexane=1:5), the solution was poured into water (30 mL), and then the resultant solution was extracted with ethyl acetate (20 mL×3). Organic layer was washed with water (30 mL×2) and saturated saline solution (30 mL). After the obtained organic layer was dried using magnesium sulfate, the solvent was distilled off under reduced pressure to yield colorless oil residue (70 mg). Flash column chromatography (ethyl acetate:n-hexane=1:5) yielded colorless oil of Intermediate J1 (67 mg, 71%).

$^1$H NMR (300 MHz, CDCl$_3$) δ 8.84 (d, 1 H, J=2.5 Hz, Ar—H), 7.77 (dd, 1 H, J=9.0 and 2.5 Hz, Ar—H), 7.43 (m, 5 H, Ar—H), 7.29 (d, 1 H, J=8.0 Hz, Ar—H), 6.80 (dd, 1 H, J=8.0 and 2.0 Hz, Ar—H), 6.73 (d, 1 H, J=2.0 Hz, Ar—H), 6.20 (d, 1 H, J=9.0 Hz, Ar—H), 5.05 (s, 2 H, CH$_2$Ph), 4.01 (q, 2 H, J=7.0 Hz, NCH$_2$CH$_3$), 3.85 (s, 3 H, CO$_2$CH$_3$), 3.43 (sept, 1 H, J=7.0 Hz, CH(CH$_3$)$_2$), 1.28 (d, 6 H, J=7.0 Hz, CH(CH$_3$)$_2$), 1.20 (t, 3 H, J=7.0 Hz, NCH$_2$CH$_3$).

2) Synthesis of Target Compound 13a

Intermediate J1 (67 mg, 0.17 mmol) was dissolved in methanol (3.0 mL), then 2 N aqueous sodium hydroxide (3.0 mL) was added, and the resultant solution was stirred for 3 hours on water bath at 60° C. After the completion of the reaction was confirmed on TLC plates (ethyl acetate:n-hexane=1:3), the solution was poured into saturated ammonium chloride aqueous solution (20 mL), and then the resultant solution was extracted with ethyl acetate (20 mL×3). After the obtained organic layer was washed with water (30 mL×2) and saturated saline solution (30 mL), the washed layer was then dried using magnesium sulfate. The solvent was distilled off under reduced pressure to yield colorless residue of the target compound 13a (55 mg, 83%).

$^1$H NMR (300 MHz, DMSO-d6) δ: 12.51 (br s, 1 H, CO$_2$H), 8.67 (d, 1 H, J=2.5 Hz, Ar—H), 7.76 (dd, 1 H, J=9.0 and 2.5 Hz, Ar—H), 7.46-7.33 (m, 5 H, Ar—H), 7.32 (d, 1 H, J=8.0 Hz, Ar—H), 6.95 (d, 1 H, J=2.0 Hz, Ar—H), 6.85 (dd, 1 H, J=8.0 and 2.0 Hz, Ar—H), 6.21 (d, 1 H, J=9.0 Hz, Ar—H), 5.13 (s, 2 H, CH$_2$Ph), 3.97 (q, 2 H, J=7.0 Hz, NCH$_2$CH$_3$), 3.32 (sept, 1 H, J=7.0 Hz, CH(CH$_3$)$_2$), 1.22 (d, 6 H, J=7.0 Hz, CH(CH$_3$)$_2$), 1.12 (t, 3 H, J=7.0 Hz, NCH$_2$CH$_3$).

Example 11

Synthesis of Target Compound 13b

The scheme of production method in this Example will be shown in FIG. 7.

1) Synthesis of Intermediate K1

Intermediate I1 (59 mg, 0.2 mmol) was dissolved in anhydrous N,N-dimethylformamide (3.0 mL), then potassium carbonate (69 mg, 0.5 mmol), an appropriate amount of potassium iodide and (2-bromoethyl)benzene (68 μL, 0.5 mmol) were added, and the resultant solution was heated to 60° C. for 17 hours with stirring under argon atmosphere. After the completion of the reaction was confirmed on TLC plates (ethyl acetate:n-hexane=1:6), the solution was poured into water (30 mL), and then the resultant solution was extracted with ethyl acetate (20 mL×3). Organic layer was washed with water (30 mL×2) and saturated saline solution (30 mL). After the obtained organic layer was dried using magnesium sulfate, the solvent was distilled off under reduced pressure to yield colorless oil residue (87 mg). Flash column chromatography (ethyl acetate:n-hexane=1:15→1:6) yielded colorless oil of Intermediate K1 (27 mg, 35%).

$^1$H NMR (300 MHz, CDCl$_3$) δ 8.83 (d, 1 H, J=2.5 Hz, Ar—H), 7.78 (dd, 1 H, J=9.0 and 2.5 Hz, Ar—H), 7.32-7.22 (m, 6 H, Ar—H), 6.76 (dd, 1 H, J=8.0 and 2.0 Hz, Ar—H), 6.63 (d, 1 H, J=2.0 Hz, Ar—H), 6.22 (d, 1 H, J=9.0 Hz, Ar—H), 4.12 (t, 2 H, J=6.5 Hz, OCH$_2$CH$_2$Ph), 4.00 (q, 2 H, J=7.0 Hz, NCH$_2$CH$_3$), 3.85 (s, 3 H, CO$_2$CH$_3$), 3.31 (sept, 1 H, J=7.0 Hz, CH(CH$_3$)$_2$), 3.11 (t, 2 H, J=6.5 Hz, OCH$_2$CH$_2$Ph), 1.21 (t, 3 H, J=7.0 Hz, NCH$_2$CH$_3$), 1.21 (d, 6 H, J=7.0 Hz, CH(CH$_3$)$_2$).

2) Synthesis of Target Compound 13b

Intermediate K1 (27 mg, 0.07 mmol) was dissolved in methanol (3.0 mL), then 2 N aqueous sodium hydroxide (3.0 mL) was added, and the resultant solution was stirred for 2 hours on water bath at 60° C. After the completion of the reaction was confirmed on TLC plates (ethyl acetate:n-hexane=1:3), the solution was poured into saturated ammonium chloride aqueous solution (20 mL), and then the resultant solution was extracted with ethyl acetate (20 mL×3). After the obtained organic layer was washed with water (20 mL×2) and saturated saline solution (20 mL), the washed layer was then dried using magnesium sulfate. The solvent was distilled off under reduced pressure to yield colorless residue (25 mg, 89%) of the target. Recrystallization (methanol) yielded colorless needle crystal of the target compound 13b (6 mg, 21%).

$^1$H NMR (300 MHz, DMSO-d6) δ: 12.47 (br s, 1 H, CO$_2$H), 8.66 (d, 1 H, J=2.5 Hz, Ar—H), 7.77 (dd, 1 H, J=9.0 and 2.5 Hz, Ar—H), 7.31-7.21 (m, 5 H, Ar—H), 7.26 (d, 1 H, J=8.0 Hz, Ar—H), 6.85 (d, 1 H, J=2.0 Hz, Ar—H), 6.80 (dd, 1 H, J=8.0 and 2.0 Hz, Ar—H), 6.23 (d, 1 H, J=9.0 Hz, Ar—H), 4.17 (t, 2 H, J=6.5 Hz, OCH$_2$CH$_2$Ph), 3.97 (q, 2 H, J=7.0 Hz, NCH$_2$CH$_3$), 3.19 (sept, 1 H, J=7.0 Hz, CH(CH$_3$)$_2$), 3.04 (t, 2 H, J=6.5 Hz, OCH$_2$CH$_2$Ph), 1.13 (d, 6 H, J=7.0 Hz, CH(CH$_3$)$_2$), 1.13 (t, 3 H, J=7.0 Hz, NCH$_2$CH$_3$).

Example 12

Synthesis of Target Compound 13c

The scheme of production method in this Example will be shown in FIG. 7.
1) Synthesis of Intermediate L1

Intermediate I1 (77 mg, 0.2 mmol) was dissolved in anhydrous N,N-dimethylformamide (3.0 mL), then potassium carbonate (69 mg, 0.5 mmol), an appropriate amount of potassium iodide and 3-bromo-2-methyl propene (50 μL, 0.5 mmol) were added, and the resultant solution was heated to 60° C. for 4 hours with stirring under argon atmosphere. After the completion of the reaction was confirmed on TLC plates (ethyl acetate:n-hexane=1:5), the solution was poured into water (60 mL), and then the resultant solution was extracted with ethyl acetate (20 mL×3). Organic layer was washed with water (40 mL) and saturated saline solution (40 mL). After the obtained organic layer was dried using magnesium sulfate, the solvent was distilled off under reduced pressure to yield brown oil residue (92 mg). Flash column chromatography (ethyl acetate:n-hexane=1:6) yielded colorless oil of Intermediate L1 (60 mg, 71%).

$^1$H NMR (300 MHz, CDCl$_3$) δ 8.85 (d, 1 H, J=2.5 Hz, Ar—H), 7.80 (dd, 1 H, J=9.0 and 2.5 Hz, Ar—H), 7.27 (d, 1 H, J=8.0 Hz, Ar—H), 6.79 (dd, 1 H, J=8.0 and 2.0 Hz, Ar—H), 6.66 (d, 1 H, J=2.0 Hz, Ar—H), 6.25 (d, 1 H, J=9.0 Hz, Ar—H), 5.10 (s, 1 H, OCH$_2$C(CH$_2$)CH$_3$), 4.99 (s, 1 H, OCH$_2$C(CH$_2$)CH$_3$), 4.39 (s, 2 H, OCH$_2$C(CH$_2$)CH$_3$), 4.03 (q, 2 H, J=7.0 Hz, NCH$_2$CH$_3$), 3.86 (s, 3 H, CO$_2$CH$_3$), 3.39 (sept, 1 H, J=7.0 Hz, CH(CH$_3$)$_2$), 1.84 (s, 3 H, OCH$_2$C(CH$_2$)CH$_3$), 1.27 (d, 6 H, J=7.0 Hz, CH(CH$_3$)$_2$), 1.23 (t, 3 H, J=7.0 Hz, NCH$_2$CH$_3$).
2) Synthesis of Target Compound 13c Intermediate L1 (60 mg, 0.17 mmol) was dissolved in methanol (3.0 mL), then 2 N aqueous sodium hydroxide (3.0 mL) was added, and the resultant solution was stirred for 3 hours on water bath at 60° C. After the completion of the reaction was confirmed on TLC plates (ethyl acetate:n-hexane=1:3), the solution was poured into saturated ammonium chloride aqueous solution (20 mL), and then the resultant solution was extracted with ethyl acetate (20 mL×3). After the obtained organic layer was washed with water (20 mL×2) and saturated saline solution (30 mL), the washed layer was then dried using magnesium sulfate. The solvent was distilled off under reduced pressure to yield colorless residue (60 mg, 95%) of the target. Recrystallization (methanol) yielded colorless needle crystal of the target compound 13c (32 mg, 51%).

$^1$H NMR (300 MHz, DMSO-d6) δ 12.49 (br s, 1 H, CO$_2$H), 8.67 (d, 1 H, J=2.5 Hz, Ar—H), 7.78 (dd, 1 H, J=9.0 and 2.5 Hz, Ar—H), 7.51 (d, 1 H, J=8.0 Hz, Ar—H), 6.84-6.81 (m, 2 H, Ar—H), 6.25 (d, 1 H, J=9.0 Hz, Ar—H), 5.08 (s, 1 H, OCH$_2$C(CH$_2$)CH$_3$), 4.96 (s, 1 H, OCH$_2$C(CH$_2$)CH$_3$), 4.47 (s, 2 H, OCH$_2$C(CH$_2$)CH$_3$), 3.98 (q, 2 H, J=7.0 Hz, NCH$_2$CH$_3$), 3.30 (sept, 1 H, J=7.0 Hz, CH(CH$_3$)$_2$), 1.78 (s, 3 H, OCH$_2$C(CH$_2$)CH$_3$), 1.22 (d, 6 H, J=7.0 Hz, CH(CH$_3$)$_2$), 1.14 (t, 3 H, J=7.0 Hz, NCH$_2$CH$_3$).

Example 13

Synthesis of Target Compound 13d

The scheme of production method in this Example will be shown in FIG. 7.
1) Synthesis of Intermediate M1

Intermediate I1 (89 mg, 0.3 mmol) was dissolved in anhydrous N,N-dimethylformamide (3.0 mL), then potassium carbonate (69 mg, 0.5 mmol), an appropriate amount of potassium iodide and 1-bromo-3-methyl-2-butene (59 μL, 0.5 mmol) were added, and the resultant solution was heated to 60° C. for 17 hours with stirring under argon atmosphere. After the completion of the reaction was confirmed on TLC plates (ethyl acetate:n-hexane=1:6), the solution was poured into water (30 mL), and then the resultant solution was extracted with ethyl acetate (20 mL×3). Organic layer was washed with water (30 mL×2) and saturated saline solution (30 mL). After the obtained organic layer was dried using magnesium sulfate, the solvent was distilled off under reduced pressure to yield colorless oil residue (76 mg). Flash column chromatography (ethyl acetate:n-hexane=1:7) yielded colorless oil of Intermediate M1 (50 mg, 50%).

$^1$H NMR (300 MHz, CDCl$_3$) δ 8.85 (d, 1 H, J=2.5 Hz, Ar—H), 7.79 (dd, 1 H, J=9.0 and 2.5 Hz, Ar—H), 7.25 (d, 1 H, J=8.0 Hz, Ar—H), 6.77 (dd, 1 H, J=8.0 and 2.0 Hz, Ar—H), 6.66 (d, 1 H, J=2.0 Hz, Ar—H), 6.25 (d, 1 H, J=9.0 Hz, Ar—H), 5.45 (m, 1 H, OCH$_2$CHC(CH$_3$)$_2$), 4.48 (d, 2 H, J=6.5 Hz, OCH$_2$CHC(CH$_3$)$_2$), 4.03 (q, 2 H, J=7.0 Hz, NCH$_2$CH$_3$), 3.86 (s, 3 H, CO$_2$CH$_3$), 3.35 (sept, 1 H, J=7.0 Hz, CH(CH$_3$)$_2$), 1.77 (s, 3 H, OCH$_2$CHC(CH$_3$)$_2$), 1.69 (s, 3 H, OCH$_2$CHC(CH$_3$)$_2$), 1.24 (d, 6 H, J=7.0 Hz, CH(CH$_3$)$_2$).
2) Synthesis of Target Compound 13d Intermediate M1 (50 mg, 0.14 mmol) was dissolved in methanol (3.0 mL), then 2 N aqueous sodium hydroxide (3.0 mL) was added, and the resultant solution was stirred for 3 hours on water bath at 60° C. After the completion of the reaction was confirmed on TLC plates (ethyl acetate:n-hexane=1:3), the solution was poured into saturated ammonium chloride aqueous solution (20 mL), and then the resultant solution was extracted with ethyl acetate (20 mL×3). After the obtained organic layer was washed with water (30 mL×2) and saturated saline solution (30 mL), the washed layer was then dried using magnesium sulfate. The solvent was distilled off under reduced pressure to yield colorless residue (50 mg, q.y.) of the target. Recrystallization (methanol) yielded colorless needle crystal of the target compound 13d (13 mg, 25%).

$^1$H NMR (300 MHz, DMSO-d6) δ 12.46 (br s, 1 H, CO$_2$H), 8.67 (d, 1 H, J=2.5 Hz, Ar—H), 7.78 (dd, 1 H, J=9.0 and 2.5 Hz, Ar—H), 7.28 (d, 1 H, J=8.0 Hz, Ar—H), 6.85 (d, 1 H, J=2.0 Hz, Ar—H), 6.81 (dd, 1 H, J=8.0 and 2.0 Hz, Ar—H), 6.25 (d, 1 H, J=9.0 Hz, Ar—H), 5.41 (t, 1 H, J=6.5 Hz, OCH$_2$CHC(CH$_3$)$_2$), 4.53 (d, 2 H, J=6.5 Hz, OCH$_2$CHC(CH$_3$)$_2$), 3.98 (q, 2 H, J=7.0 Hz, NCH$_2$CH$_3$), 3.25 (sept, 1 H, J=7.0 Hz, CH(CH$_3$)$_2$), 1.73 (s, 3 H, OCH$_2$CHC(CH$_3$)$_2$), 1.66 (s, 3 H, OCH$_2$CHC(CH$_3$)$_2$), 1.19 (d, 6 H, J=7.0 Hz, CH(CH$_3$)$_2$), 1.14 (t, 3 H, J=7.0 Hz, NCH$_2$CH$_3$).

Comparative Example

Formula XIII (PA024):

[Compound 13]

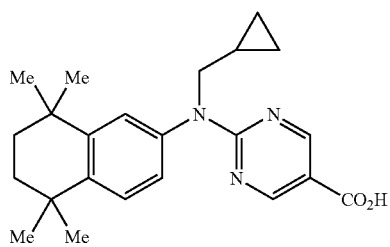

Formula (XIII)

Formula XIV (SR11237):

[Compound 14]

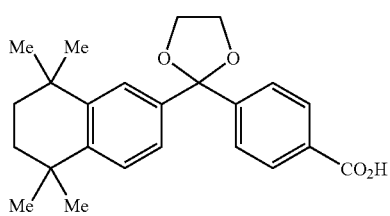

Formula (XIV)

Formula XV (HX630):

[Compound 15]

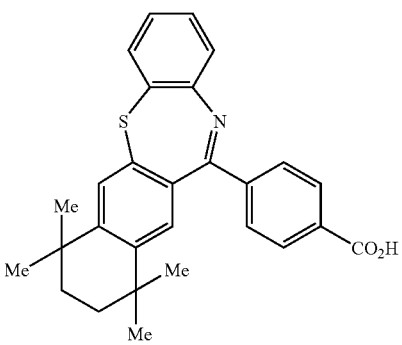

Formula (XV)

Formula XVI (LGD1069):

[Compound 16]

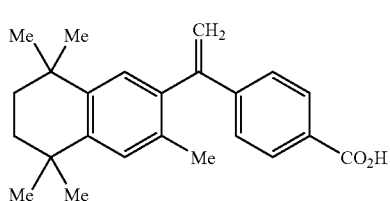

Formula (XVI)

TABLE 3

| Compound | CLogP |
|---|---|
| PA024 | 7.18 |
| SR11237 | 6.40 |
| HX630 | 9.18 |
| LGD1069 | 8.19 |

Experimental Example 1

Activity Evaluation Method 1

Human leukemia cell strain HL-60 differentiates into granulocytes (neutrophils) to come to have an ability to express active oxygen. When TPA (12-o-tetradecanoyl-phorbol-13-acetate) stimulation causes active oxygen to be produced in this cell and reduces NBT (Nitro Blue Tetrazolium), the cells are stained blue. A method for measuring differentiation inducibility of cells into granulocytes by using this principle is referred to as NBT reduction method. So, the differentiation inducibility of the synthesized compound was measured by NBT reduction method.

Fetal bovine serum (FBS) was added to RPMI-1640 media into 10 v/v % and further antibiotics (penicillin and streptomycin) added, and that was used as a growth medium to culture human leukemia cell strain HL-60. Cell subculturing was conducted using a culture flask by maintaining and sub-culturing cells in a incubator containing 5% $CO_2$ so as not to allow the cell density to exceed 100 cells/mL, and was used for experiment (Nonpatent document No. 16).

1) Agents and Compounds

For the synthesized compound of the present Experimental Example represented by the general formula XII and the compound (PA024) of Comparative Example represented by formula XIII, their CLogPs indicating lipid solublity were calculated by ChemDraw™, which is a program for illustrating chemical structure, and their values were given in Tables 2 and 3. As a result, the compound of the present invention was confirmed to have a lower lipid-solubility than those of each compound represented by Comparative Examples.

Each compound was dissolved in dimethylsulfoxide (DMSO) into 20 mM to prepare a stock solution. NBT was prepared into 0.2 w/v % by using PBS (−) 2 hours before use and incubated at 37° C. TPA was dissolved in ethanol (EtOH) into 2 mg/mL to prepare a stock solution. This TPA solution was prepared into 20 μg/mL by using PBS (−) at the time of use.

2) Method

To a cell solution in which human leukemia cell strain HL-60 ($8\times10^4$ cells/mL) was suspended in 2 ml of growth medium, PA024 and each compound were added to final concentrations of 10 μM and 1 μM respectively, and were then cultured in the incubator containing 5% $CO_2$ for four days. The action of RXR agonist is enhanced by the combined use of that and RAR agonist. Therefore, when synergistic activity was evaluated, Am80, the known RAR agonist, was added to a final concentration of 0.33 nM and was cultured likewise (Nonpatent document No. 16). After four days cultivation, cells were collected by centrifugation (4° C., 1500 rpm, 5 minutes). After these cells were seeded onto 1 mL of a fresh growth medium, then 1 mL of 0.2 w/v % NBT solution and 20 μl of 20 μg/ml of TPA solution were added, and incubation was carried out in the incubator containing 5% $CO_2$ at 37° C. for 30 minutes. Then, stained cell number and total cell number were counted on a cell counter. Meanwhile, the measurement was conducted three times by counting 200 cells or more at a time and a differentiation inducing rate was calculated from a mean value obtained by averaging them.

The test result described above was shown in Table 4 below. In Table 4, a) $EC_{50}$ of retinoid activity showed a concentration giving the half of maximum differentiation inducing rate in HL-60 differentiation induction under the test compound alone. Meanwhile, "inert" means that differentiation inducibility can not be observed even at 10 μM. Likewise, b) BA (bioactivity) (%) refers to the maximum differentiation inducing rate relative to the total cell number in this test. Likewise, c) $SEC_{50}$ is a retinoid synergistic activity and is referred to as a concentration giving the half of the maximum differentiation inducing rate in HL-60 differentiation induction of the test compound when Am80, which is widely known as a retinoid agonist, is present at $3.3\times10^{-10}$M. Meanwhile, the differentiation inducing rate of HL-60 is between 2 and 4% when Am80 is present alone at this concentration.

TABLE 4

| Compound | R[7] | R[6] | R[3] | X[1] | Y[1] | Y[2] | Retinoid activity EC$_{50}$(nM)[a] | BA(%)[b] | Retinoid synergistic activity SEC$_{50}$(nM)[c] | BA(%)[b] |
|---|---|---|---|---|---|---|---|---|---|---|
| PA024 | | | | | | | Inert[a] | — | 3 | 80 |
| 1a(NEt-3IP) | O-i-Pr | i-Pr | Et | CH | N | CH | >10000 | 4 | 10 | 80 |
| 1b | O-i-Pr | i-Pr | Ms | CH | N | CH | >10000 | 44 | 900 | 63 |
| 1c | O-i-Pr | i-Pr | H | CH | N | CH | >10000 | 24 | 4500 | 63 |
| 2a | O-n-Pr | i-Pr | Et | CH | N | CH | >10000 | 4 | 23 | 74 |
| 2b | O-n-Pr | i-Pr | Ms | CH | N | CH | >10000 | 50 | 800 | 63 |
| 2c | O-n-Pr | i-Pr | H | CH | N | CH | >10000 | 50 | 4300 | 60 |
| 3a(NEt-3IB) | O-i-Bu | i-Pr | Et | CH | N | CH | >10000 | — | 22 | 81 |
| 4a(NEt-4IP) | i-Pr | O-i-Pr | Et | CH | N | CH | >10000 | — | 23 | 64 |
| 4c | i-Pr | O-i-Pr | H | CH | N | CH | >10000 | 24 | >10000 | 29 |
| 5c | i-Pr | O-n-Pr | H | CH | N | CH | >10000 | 3 | >10000 | 15 |
| 6a(PEt-3IP) | O-i-Pr | i-Pr | Et | CH | N | N | >10000 | 3 | 12 | 87 |

From the results above, the compound of the present invention exhibited no less synergistic activity (promoting action for Am80 differentiation-induction) for HL-60 cells than PA024, which is an existing compound for regulating cell differentiation induction. Further, it was confirmed that retinoid synergistic activation effect obtained from acting together with Am80 is extremely high.

Experimental Example 2

Activity Evaluation Method 2

Most of nuclear receptors are transcription factors associated with regulating transcription, so that reporter gene assay is conducted as a means of measuring its transcription activity. An expression plasmid for RXR receptor protein and a reporter plasmid were introduced into cells such as COS-1 cells and HeLa cells to cause overexpression. And, when RXR agonist is bound to the receptor, transcription is induced in a ligand dependent manner, and a protein which is referred to as fusion protein downstream is produced. The binding of this fusion protein to the binding site on the reporter plasmid initiates the transcription to produce luciferase downstream. RXR agonistic activity was measured by measuring this luciferase activity.

Dulbecco's Modified Eagle MEM medium (DMEM) was used as growth medium. First, the medium was prepared by dissolving 9.5 g of DMEM powder in 1 L of Milli-Q water, applying it to autoclave (121° C., for 15 minutes), then cooling it to room temperature, adding an inactivated fetal bovine serum (FBS) into 10% (v/v), further adding 10 mL of 10% NaHCO$_3$, which was previously applied to autoclave, and then adding 10 mL of filter-sterilized L-glutamine thereto.

Passage was conducted by removing culture supernatant from the cell culture grown in a 100 mm culture dish, collecting cells by trypsinization, centrifuging at 1000 rpm at 4° C. for 3 minutes, then dispersing cells by adding growth medium and growing them in a 100 mm culture dish (15 mL of growth medium) at 37° C. in the presence of 5% CO$_2$.

Transformation was conducted using Effectene™ Transfection Reagent (QIAGEN). Further, Luciferase Assay System was used for evaluating luciferase activity. Am80 was used for the positive control of RAR, and 9-cis retinoic acid was used for the positive control of RXR. They were dissolved in DMSO for use as a stock solution and measured on every plate to be assayed. Further, ATRA (1 μM) was used for the internal control of RAR, and PA024 (1 μM) was used for that of RXR.

Method

On day 1: COS-1 cells were seeded along with 15 mL of growth medium in a 60 mm culture dish at 50×10$^4$ cells and were cultured over night.

On day 2: Transformation was conducted by lipofection using Effectene™ Transfection Reagent.

On day 3: 16 to 18 hours later, the culture supernatant was removed, cells were collected by trypsinization, centrifugation was conducted at 1000 rpm at 4° C. for 3 minutes, then cells were dispersed by adding growth medium, and then the cells were seeded on a 96-well white plate at 2.0×10$^4$ cells/well. Then, each compound was added at DMSO concentration of 1% or below.

On day 4: 24 hours later, 25 μL of the supernatant was used for SEAP measurement, and the rest cell-containing solution was used for measuring luciferase activity.

Of the test results described above, the results relating to RXR was shown in Table 5 below. In Table 5, a) EC$_{50}$ indicated a concentration giving the half of the maximum transcriptional activation potential. Likewise, b) BA (bioactivity) (%) indicates relative maximum transcriptional activation potential when PA024 (1 μM) is 100%. Likewise, c) LGD1069 referred to Nonpatent document No. 17.

Result

TABLE 5

| Compd. | OR[7] | Y[2] | RXRα EC$_{50}$ (nM) | RXRα E$_{max}$ (%) | RXRβ EC$_{50}$ (nM) | RXRβ E$_{max}$ (%) | RXRγ EC$_{50}$ (nM) | RXRγ E$_{max}$ (%) | CLogP |
|---|---|---|---|---|---|---|---|---|---|
| NEt-3IP (1a) | 3'-Oi-Pr | CH | 27 | 130 | 35 | 110 | >380 | >88 | 5.61 |
| NEt-3IB (3a) | 3'-Oi-Bu | CH | 0.77 | 110 | 18 | 140 | 3.0 | 100 | 6.23 |
| NEt-4IP (4a) | 4'-Oi-Pr | CH | >660 | >110 | >1300 | >80 | >350 | >81 | 5.61 |
| PEt-3IP (6a) | 3'-Oi-Pr | N | 6.0 | 110 | 18 | 100 | >58 | 105 | 4.89 |
| PEt-3IB (7a) | 3'-Oi-Bu | N | 2.9 | 110 | 7.3 | 140 | 4.9 | 105 | 5.50 |
| PA024 | — | — | 3.0 | 100 | 24 | 100 | 11 | 100 | 7.23 |
| LGD1069 | — | — | 3.3 | 100 | 4.3 | 110 | 2.8 | 100 | 8.23 |

EC$_{50}$ was determined by volume/reaction curves. RXR activity was standardized by PA024 (1 μM).

From the results above, the compound of the present invention exhibited more excellent transcription regulation activity (namely, expression of reporter protein through an RXR subtype) than LGD1069 (also known as bexarotene), which is an existing RXR agonist. Further, it was observed that the selectivity of compound 1a (NEt-3IP) for RXRα/β was 10 times or more than that for RXRγ (RXRα/β dual agonist).

Experimental Example 3

Activity Evaluation Method 3: Histone Deacetylase (HDAC) Inhibitory Activity
Method
HDAC inhibitory activity was evaluated for compounds represented by formulae XVII and XVIII, through the use of HDAC Activity/Inhibitor Screening Assay Kit supplied by Cayman and according to that protocol.

[Compound 17]

Formula (XVII)

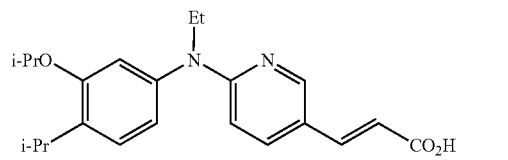

[Compound 18]

Formula (XVIII)

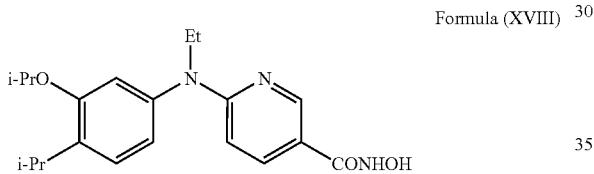

Figure 8:
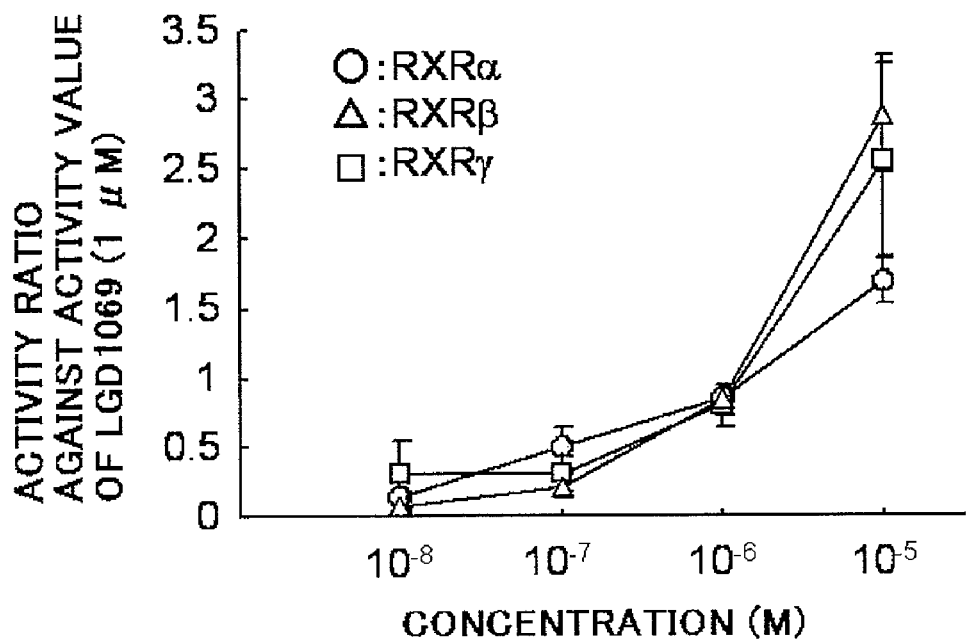
FIG. 8 shows the results of inhibitory activity against histone deacetylase in Experimental Example 3.

Results
Regarding HDAC inhibitory activity of compound XVII, activity inhibition rate was 78% at 100 μM. Further, IC50 of HDAC inhibitory activity of compound XVIII was 2.5 pMd. Meanwhile, RXR activity of this compound was as shown in FIG. 8.

Experimental Example 4

Figure 9:
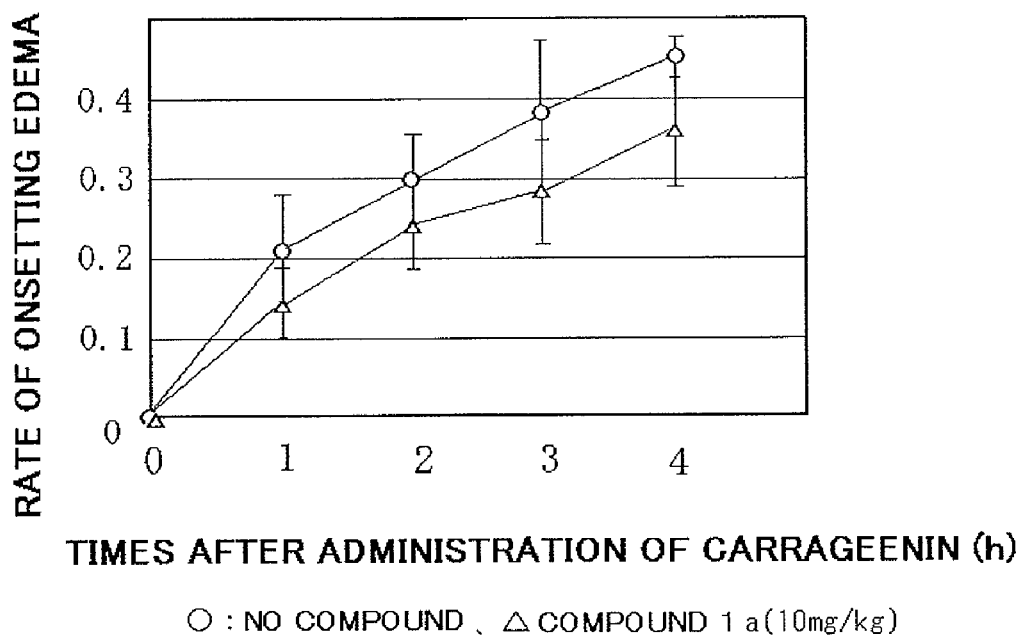
FIG. 9 shows the results of carrageenin edema tests in Experimental Example 4.

Anti-Inflammation Action (Carrageenin Edema Test)
Carrageenin edema test was used for anti-inflammatory test by using rats. 10 mg/kg compound 1a (NEt-3IP) was orally administered to five rats in a group, and then 3 hours later, 1% carrageenin solution, which was an edema-inducing substance, was subcutaneously administered to the hind foot pads (0.1 mL/rat). Then, 1, 2, 3 and 4 hours after that, the thickness of edema of the hind foot pads was measured. As a result, as shown in FIG. 9, it was revealed that the administration of compound 1a (NEt-3IP) inhibited the onset of edema induced by carrageenin. The rate of inhibiting edema was 27% 3 hours after the administration of carrageenin.
Industrial Applicability
As described in detail above, this compound binds to retinoid X receptor (RXR), which is one of nuclear receptors, and exerts its action. While the lipid-solublity of the compound of the present invention was significantly reduced as compared with existing RXR ligand, excellent RXR agonistic action and further an action of enhancing retinoid differentiation inducibility through that RXR agonistic action were confirmed. Further, a compound having more selectivity for RXRα than for RXRγ was also found. Since RXR forms heterodimers with various nuclear receptors and participates in the regulation of DNA transcription, RXR exerts synergistic or antagonistic action against nuclear receptors such as retinoic acid receptor (RAR), vitamin D receptor (VDR), and PPAR that draws attention as an target in developing therapeutic agents for diabetes and obesity. Further, since the compounds of the present invention can be expected for anticancer action, and also actions as therapeutic agents for diabetes, hair restorers and anti-inflammatory agents or action enhancers for agents having such actions, they can be used for such medications. Further, they can be used as biochemistry test reagents.

The invention claimed is:

1. A compound represented by the general Formula I shown or salt thereof:

Formula (I)

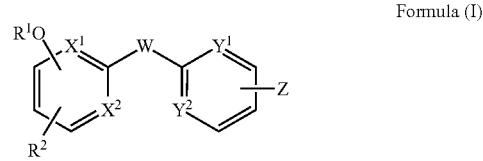

wherein,
R$^1$ and R$^2$ are independently selected from the group consisting of straight or branched, alkyl groups wherein positions of R$^1$O and R$^2$ are selected from:
  R$^1$O is in the para position with respect to X$^2$, and R$^2$ is in the meta position with respect to X$^1$ and X$^2$; or
  R$^1$O is in the meta position with respect to X$^1$ and X$^2$, and R$^2$ is in the para position with respect to X$^2$)
W is NR$^3$ or CR$^3$; wherein R$^3$ is selected from a hydrogen, straight or branched, or cyclic group,
X$^1$ is CH,
X$^2$ is selected from CH, CR$^4$ or N,
R$^4$ is selected from straight, branched or cyclic, unsubstituted or substituted alkyl, alkenyl, alkynyl, alkoxy groups, a halogen, a nitro group and an amino group,
Y$^1$ and Y$^2$ are independently selected from CH or N, and
Z is selected from —COOH, —CH=CH—COOH, —CONHOH, or —CH=CH—CONHOH, and Z is in the meta position with respect to Y$^1$ and Y$^2$.

2. A compound according to claim 1, wherein W is NR$^3$.
3. A compound according to claim 1, wherein X$^2$ is CH.
4. A compound according to claim 2, wherein X$^2$ is CH.
5. A compound according to claim 1, wherein R$^1$O is in the para position with respect to X$^2$, and R$^2$ is in the meta position with respect to X$^1$ and X$^2$.
6. A compound according to claim 2, wherein R$^1$O is in the para position with respect to X$^2$, and R$^2$ is in the meta position with respect to X$^1$ and X$^2$.
7. A compound according to claim 3, wherein R$^1$O is in the para position with respect to X$^2$, and R$^2$ is in the meta position with respect to X$^1$ and X$^2$.
8. A compound according to claim 1, wherein R$^1$O is in the meta position with respect to X$^1$ and X$^2$, and R$^2$ is in the para position with respect to X$^2$.
9. A compound according to claim 2, wherein R$^1$O is in the meta position with respect to X$^1$ and X$^2$, and R$^2$ is in the para position with respect to X$^2$.
10. A compound according to claim 3, wherein R$^1$O is in the meta position with respect to X$^1$ and X$^2$, and R$^2$ is in the para position with respect to X$^2$.

11. A compound according to claim 1, wherein both of $Y^1$ and $Y^2$ are N.

12. A compound according to claim 2, wherein both of $Y^1$ and $Y^2$ are N.

13. A compound according to claim 3, wherein both of $Y^1$ and $Y^2$ are N.

14. A compound according to claim 1, wherein $Y^1$ is N, and $Y^2$ is CH.

15. A compound according to claim 2, wherein $Y^1$ is N, and $Y^2$ is CH.

16. A compound according to claim 3, wherein $Y^1$ is N, and $Y^2$ is CH.

17. A pharmaceutical composition comprising a compound according to claim 1.

* * * * *